US012797619B2

(12) United States Patent
Xin et al.

(10) Patent No.: US 12,797,619 B2
(45) Date of Patent: Nov. 17, 2026

(54) IMPLANTABLE LEADLESS BIOSTIMULATORS AND METHODS FOR USE THEREWITH

(71) Applicant: Pacesetter, Inc., Sylmar, CA (US)

(72) Inventors: Xiyao Xin, Northridge, CA (US); Shiloh Sison, Alameda, CA (US); Xi Lin Chen, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 115 days.

(21) Appl. No.: 19/089,382

(22) Filed: Mar. 25, 2025

(65) Prior Publication Data

US 2025/0345614 A1 Nov. 13, 2025

Related U.S. Application Data

(60) Provisional application No. 63/645,793, filed on May 10, 2024.

(51) Int. Cl.

| | |
|---|---|
| ***A61N 1/368*** | (2006.01) |
| ***A61N 1/05*** | (2006.01) |
| ***A61N 1/36*** | (2006.01) |
| ***A61N 1/375*** | (2006.01) |
| ***A61N 1/378*** | (2006.01) |

(52) U.S. Cl.

CPC ........... *A61N 1/368* (2013.01); *A61N 1/0558* (2013.01); *A61N 1/0565* (2013.01); *A61N 1/0573* (2013.01); *A61N 1/36128* (2013.01); *A61N 1/3756* (2013.01); *A61N 1/378* (2013.01)

(58) Field of Classification Search

CPC .... A61N 1/368; A61N 1/0558; A61N 1/0565; A61N 1/0573; A61N 1/36128; A61N 1/3756; A61N 1/378; A61N 1/37217; A61N 1/36125; A61N 1/37288; A61N 1/37512; A61N 1/37518

See application file for complete search history.

(56) References Cited

U.S. PATENT DOCUMENTS

| | | | |
|---|---|---|---|
| 7,212,870 | B1 | 5/2007 | Helland |
| 10,583,300 | B2 | 3/2020 | Li et al. |

(Continued)

OTHER PUBLICATIONS

Response to Extended European Search Report dated Dec. 12, 2025, European Patent Application No. 25167315.8-1122.

(Continued)

*Primary Examiner* — Jonathan T Kuo
(74) *Attorney, Agent, or Firm* — Pearl Cohen LLP

(57) ABSTRACT

Implantable leadless biostimulators and related methods are described. The implantable leadless biostimulator comprises first, second and third electrodes, and also includes circuitry configured to cause a first set of the electrodes, which includes the first electrode and the third electrode, but does not include the second electrode, to be used during first periods of time to deliver stimulation pulses to the patient tissue. The circuitry is also configured to cause a second set of the electrodes, which includes the second electrode and the third electrode, to be used during second periods of time to at least one of transmit conductive communication pulses to, or receive conductive communication pulses from, one or more other devices. The second set of electrodes optionally includes the first electrode electrically connected to the second electrode.

27 Claims, 15 Drawing Sheets

(56) References Cited

U.S. PATENT DOCUMENTS

| | | | | |
|---|---|---|---|---|
| 11,097,116 | B2 * | 8/2021 | Min | A61N 1/37288 |
| 11,541,243 | B2 | 1/2023 | Eby et al. | |
| 2006/0122682 | A1 | 6/2006 | Sommer et al. | |
| 2015/0057721 | A1 * | 2/2015 | Stahmann | A61N 1/37229 607/60 |
| 2019/0016290 | A1 | 1/2019 | Kim et al. | |
| 2020/0215336 | A1 | 7/2020 | Min et al. | |
| 2020/0368538 | A1 * | 11/2020 | Min | A61N 1/3756 |
| 2021/0069516 | A1 | 3/2021 | Muessig et al. | |
| 2021/0308472 | A1 | 10/2021 | Bornzin et al. | |
| 2023/0090496 | A1 | 3/2023 | Eby et al. | |

OTHER PUBLICATIONS

Extended European Search Report dated Aug. 21, 2025, European Patent Application No. 25167315.8-1122.

* cited by examiner

IMPLANTABLE LEADLESS BIOSTIMULATORS AND METHODS FOR USE THEREWITH

PRIORITY CLAIM

This application claims priority to U.S. Provisional Patent Application No. 63/645,793, filed May 10, 2024, which is incorporated herein by reference.

FIELD OF TECHNOLOGY

Embodiments described herein generally relate to implantable leadless biostimulators that are configured to produce both therapeutic stimulation pulses, for use in delivering therapy, and conductive communication pulses, for use in communicating with one or more other devices, and methods for use therewith. In certain embodiments, the implantable leadless biostimulators are also configured to receive conductive communication pulses from the one or more other devices.

BACKGROUND

Implantable medical devices (IMDs) may utilize conductive communication signals to communicate with one another, or with one or more external devices. Where conductive communication signals are transmitted from one IMD to another IMD, the conductive communication signals can be referred to as implant-to-implant (i2i) conductive communication signals. Where conductive communication signals are transmitted from an external device to an IMD (e.g., a leadless pacemaker), the conductive communication signals can also be referred to as conductive external-to-implant (e2i) communication signals, or more succinctly as conductive e2i signals. Where the external device is a programmer, the conductive e2i signals transmitted by the external programmer to the IMD can be referred to more specifically as conductive programmer-to-implant (p2i) communication signals, or more succinctly as conductive p2i signals. In other words, conductive p2i signals are a specific type of conductive e2i signals. Where the conductive communication signals are transmitted from an IMD to an external device, the conductive communication signals can also be referred to as conductive implant-to-external (i2e) communication signals, or more succinctly as conductive i2e signals. Where the external device is a programmer, the conductive i2e signals transmitted by an IMD to the external programmer can be referred to more specifically as conductive implant-to-programmer (i2p) communication signals, or more succinctly as conductive i2p signals. In other words, conductive i2p signals are a specific type of conductive i2e signals. Conductive communication signals are also referred to sometimes as conducted communication signals, and these terms are often used interchangeably. A conductive communication signal includes one or more conductive communication pulses that are transmitted through patient tissue from a transmitting device to a receiving device. The term conductive i2i communication and the term i2i conductive communication are used interchangeably herein. Similarly, the term conductive e2i communication and the term e2i conductive communication are used interchangeably herein, and the term conductive i2e communication and the term i2e conductive communication are used interchangeably herein.

Where an IMD is an implantable leadless biostimulator, such as, but not limited to a leadless pacemaker (LP), the implantable leadless biostimulator may use the same electrodes for performing stimulation (e.g., pacing), for performing sensing of an electrocardiogram (EGM), as well as for transmitting and receiving conductive communication signals. More specifically, an LP may use the same pair of electrodes (e.g., a distal tip electrode and a proximal ring or "can" electrode) to deliver stimulation (e.g., pacing) pulses for therapeutic purposes, to sense an EGM for diagnostic purposes, and to transmit and/or receive conductive communication pulses for communicative purposes. Since an implantable leadless biostimulator (e.g., LP) is quite small in size, and thus has a battery that is quite small in size, it is important to conserve as much power as possible in order to elongate battery life and thereby elongate the life of the implantable leadless biostimulator.

SUMMARY

Certain embodiments of the present technology are directed to an implantable leadless biostimulator comprises first, second and third electrodes. Each of the first and the second electrodes is located on and/or extending from a distal portion of the implantable leadless biostimulator and is configured such that a respective electrically conductive surface area thereof is configured to be in physical contact with patient tissue of a patient within which the implantable leadless biostimulator is to be implanted, and such that the electrically conductive surface area of the second electrode that is configured to be in physical contact with the patient tissue is greater than the electrically conductive surface area of the first electrode that is configured to be in physical contact with the patient tissue. The third electrode is located on a proximal portion of the implantable leadless biostimulator and electrically isolated from the first and the second electrodes. The implantable leadless biostimulator further comprises circuitry configured to cause a first set of the electrodes, which includes the first electrode and the third electrode, but does not include the second electrode, to be used during first periods of time to deliver stimulation pulses to the patient tissue. The circuitry is also configured to cause a second set of the electrodes, which includes the second electrode and the third electrode, to be used during second periods of time to at least one of transmit conductive communication pulses to, or receive conductive communication pulses from, one or more other devices. The second set of electrodes optionally includes the first electrode electrically connected to the second electrode.

Explained another way, the circuitry is configured to cause delivery of stimulation pulses to the patient tissue during first periods of time by a first set of the electrodes, which includes the first electrode and the third electrode, but does not include the second electrode; and to cause transmission of conductive communication pulses to, and/or reception of conductive communication pulses from, one or more other devices during second periods of time by a second set of the electrodes, which includes the second electrode and the third electrode. In such embodiments, the second set of electrodes optionally includes the first electrode electrically connected to the second electrode.

In accordance with certain embodiments, the first electrode comprises a distal tip electrode located at a distal end of the implantable leadless biostimulator; the second electrode comprises a fixation element extending from the distal portion of the implantable leadless biostimulator and configured to physically attach the implantable leadless biostimulator to the patient tissue, or the second electrode comprises a distal ring electrode that encircles the distal tip electrode; and the third electrode comprises a proximal electrode located on the proximal portion of the implantable leadless biostimulator.

In accordance with certain embodiments, a first portion of the distal tip electrode is covered by an insulator coating and a second portion of the distal tip electrode is devoid of the insulator coating in order to achieve a higher effective impedance than would be achieved if an entirety of the distal tip electrode were devoid of the insulator coating.

In accordance with certain embodiments, the implantable leadless biostimulator further comprises a battery configured to power the implantable leadless biostimulator including the circuitry thereof; wherein the second electrode comprises the fixation element; and wherein a first portion of the fixation element is covered by an insulator coating and a second portion of the fixation element is devoid of the insulator coating in order to achieve an effective impedance (e.g., within a specified range) that increases a longevity of the battery compared to if an entirety of the fixation element was devoid of the insulator coating.

In accordance with certain embodiments, the proximal electrode is provided by at least a portion of an electrically conductive housing that houses the battery; and the distal tip electrode is electrically isolated from the electrically conductive housing.

In accordance with certain embodiments, the implantable leadless biostimulator is a leadless pacemaker; the distal tip electrode is located at a distal end of the leadless pacemaker and is configured to be in physical contact with cardiac tissue; the second electrode comprises the fixation element, which is configured to physically attach the leadless pacemaker to the cardiac tissue; the proximal electrode is located on a proximal portion of the leadless pacemaker; and the electrically conductive surface area of the fixation element that is configured to be in physical contact with the cardiac tissue is greater than the electrically conductive surface area of the distal tip electrode that is configured to be in physical contact with the cardiac tissue.

In accordance with certain embodiments, the first set of the electrodes includes the distal tip electrode and the proximal electrode; and the second set of electrodes includes the fixation element or the distal ring electrode electrically connected to the distal tip electrode, and also includes the proximal electrode.

In accordance with certain embodiments, the circuitry comprises a controller and a switch. The controller is configured to: control the switch to cause the first electrode and the second electrode to be electrically disconnected from one another during the first periods of time during which stimulation pulses are to be delivered to the patient tissue using the first electrode and the third electrode; and control the switch to cause the first electrode and the second electrode be electrically connected to one another during the second periods of time during which conductive communication pulses are to be at least one of transmitted to, or received from, the one or more other devices using the first electrode and the second electrode, which are electrically connected to one another, and using the third electrode.

In accordance with certain embodiments, the implantable leadless biostimulator further comprises a pulse generator that is configured to produce both the stimulation pulses and the conductive communication pulses, wherein the circuitry comprises a controller and a switch. The controller is configured to control the switch to cause the first electrode and the third electrode to be electrically connected to output terminals of the pulse generator during the first periods of time during which stimulation pulses are to be delivered to the patient tissue using the first electrode and the third electrode. The controller is also configured to control the switch to cause the second electrode and the third electrode to be electrically connected to the output terminals of the pulse generator during the second periods of time during which the conductive communication pulses produced by the pulse generator are to be transmitted to the one or more other devices using the second electrode and the third electrode.

In accordance with certain embodiments, the implantable leadless biostimulator further comprises: a first pulse generator configured to produce the stimulation pulses; and a second pulse generator configured to produce the conductive communication pulses. The circuitry includes a controller configured to selectively activate each of the first and the second pulse generators; wherein the first electrode and the third electrode are configured to deliver the stimulation pulses produced by the first pulse generator; and wherein the second electrode and the third electrode are configured to transmit the conductive communication pulses produced by the second pulse generator. the circuitry also comprises a switch; and the controller is configured to: control the switch to cause the second electrode to be electrically disconnected from the first electrode during the first periods of time during which the stimulation pulses are to be delivered to the patient tissue using the first electrode and the third electrode; and control the switch to cause the second electrode to be electrically connected to the first electrode during the second periods of time during which the conductive communication pulses are to be at least one of transmitted to, or received from, the one or more other devices using the first electrode and the second electrode, which are electrically connected to one another, and using the third electrode.

In accordance with certain embodiments, the implantable leadless biostimulator further comprises a low frequency (LF) receiver; and a high frequency (HF) receiver. The HF receiver is normally disabled to conserve power. The LF receiver is configured to monitor for a LF wakeup pulse in a signal sensed between the first electrode and the third electrode and in response to receiving the LF wakeup pulse the LF receiver is configured to enable the HF receiver so that the HF receiver can receive HF conductive communication pulses from one of the one or more other devices. The circuitry includes a controller and a switch. The controller is configured to: control the switch to cause the second electrode to be electrically disconnected from the first electrode while the LF receiver monitors the signal sensed between the first electrode and the third electrode for the LF wakeup pulse from one of the one or more other devices; and control the switch to cause the second electrode to be electrically connected to the first electrode, in response to the LF receiver receiving the LF wakeup pulse and enabling the HF receiver so that the HF receiver can receive HF conductive communication pulses from the one of the one or more other devices in a signal sensed between the first electrode and the third electrode while the second electrode is electrically connected by the switch to the first electrode.

In accordance with certain embodiments, the one or more other devices comprises an external device; the controller is configured to: control the switch to electrically connect the second electrode to the first electrode while monitoring for one or more conductive communication pulses transmitted by the external device and while at least one frame is being conductively communicated between the implantable leadless biostimulator and the external device; and control the switch to electrically disconnect the second electrode from the first electrode while not monitoring for the one or more conductive communication pulses transmitted by the external device and while no frame is being conductively communicated between the implantable leadless biostimulator and the external device.

In accordance with certain embodiments, the implantable leadless biostimulator is a leadless neurostimulator.

Certain embodiments of the present technology are directed to methods for use by an implantable leadless biostimulator comprising first, second and third electrodes, wherein each of the first and the second electrodes is located on and/or extending from a distal portion of the implantable leadless biostimulator and is configured such that a respective electrically conductive surface area thereof is configured to be in physical contact with patient tissue of a patient within which the implantable leadless biostimulator is implanted, and such that the electrically conductive surface area of the second electrode that is configured to be in physical contact with the patient tissue is greater than the electrically conductive surface area of the first electrode that is configured to be in physical contact with the patient tissue. The third electrode is located on a proximal portion of the implantable leadless biostimulator and is electrically isolated from the first and the second electrodes.

In accordance with certain embodiments, the method comprises: using a first set of the electrodes, which includes the first electrode and the third electrode, but does not include the second electrode, during first periods of time to deliver stimulation pulses to the patient tissue; and using a second set of the electrodes, which includes the second electrode and the third electrode, during second periods of time to at least one of transmit conductive communication pulses to, or receive conductive communication pulses from, one or more other devices. The second set of electrodes optionally includes the first electrode electrically connected to the second electrode.

Explained another way, the method includes delivering stimulation pulses to the patient tissue during first periods of time by a first set of the electrodes, which includes the first electrode and the third electrode, but does not include the second electrode; and transmitting conductive communication pulses to, and/or receiving conductive communication pulses from, one or more other devices during second periods of time by a second set of the electrodes, which includes the second electrode and the third electrode. In such embodiments, the second set of electrodes optionally includes the first electrode electrically connected to the second electrode.

In accordance with certain embodiments, the first electrode comprises a distal tip electrode located at a distal end of the implantable leadless biostimulator; the second electrode comprises a fixation element extending from the distal portion of the implantable leadless biostimulator and configured to physically attach the implantable leadless biostimulator to the patient tissue, or the second electrode comprises a distal ring electrode that encircles the distal tip electrode; and the third electrode comprises a proximal electrode located on the proximal portion of the implantable leadless biostimulator.

In accordance with certain embodiments, a first portion of the distal tip electrode is covered by an insulator coating and a second portion of the distal tip electrode is devoid of the insulator coating in order to achieve a higher effective impedance than would be achieved if an entirety of the distal tip electrode were devoid of the insulator coating.

In accordance with certain embodiments, the implantable leadless biostimulator is a leadless pacemaker; the distal tip electrode is located at a distal end of the leadless pacemaker and is configured to be in physical contact with cardiac tissue; the second electrode comprises the fixation element which is configured to physically attach the leadless pacemaker to the cardiac tissue; the proximal electrode is located on a proximal portion of the leadless pacemaker; and the electrically conductive surface area of the fixation element that is in physical contact with the cardiac tissue is greater than the electrically conductive surface area of the distal tip electrode that is in physical contact with the cardiac tissue.

In accordance with certain embodiments, the first set of the electrodes includes the distal tip electrode and the proximal electrode; and the second set of electrodes includes the fixation element or the distal ring electrode electrically connected to the distal tip electrode, and also includes the proximal electrode.

In accordance with certain embodiments, the method further comprises controlling a switch to cause the first electrode and the second electrode to be electrically disconnected from one another during the first periods of time during which stimulation pulses are to be delivered to the patient tissue using the first electrode and the third electrode; and controlling the switch to cause the first electrode and the second electrode to be electrically connected to one another during the second periods of time during which conductive communication pulses are to be at least one of transmitted to, or received from, the one or more other devices using the first electrode and the second electrode, which are electrically connected to one another, and using the third electrode.

In accordance with certain embodiments, the implantable leadless biostimulator further comprises a pulse generator that is configured to produce both the stimulation pulses and the conductive communication pulses, and the method further comprises: controlling a switch to cause the first electrode and the third electrode to be electrically connected to output terminals of the pulse generator during the first periods of time during which stimulation pulses are to be delivered to the patient tissue using the first electrode and the third electrode; and controlling the switch to cause the second electrode and the third electrode to be electrically connected to the output terminals of the pulse generator during the second periods of time during which the conductive communication pulses produced by the pulse generator are to be transmitted to the one or more other devices using the second electrode and the third electrode.

In accordance with certain embodiments, the implantable leadless biostimulator further comprises a first pulse generator configured to produce the stimulation pulses, and a second pulse generator configured to produce the conductive communication pulses, and the method further comprises: selectively activating each of the first and the second pulse generators; delivering the stimulation pulses produced by the first pulse generator using the first electrode and the third electrode; and transmitting the conductive communication pulses produced by the second pulse generator using the second electrode and the third electrode.

In accordance with certain embodiments, the method further comprises: controlling a switch to cause the first electrode and the second electrode to be electrically disconnected from one another during the first periods of time during which the stimulation pulses produced by the first pulse generator are to be delivered to the patient tissue using the first electrode and the third electrode; and controlling the switch to cause the first electrode and the second electrode to be electrically connected to one another during the second periods of time during which the conductive communication pulses produced by the second pulse generator are to be transmitted to the one or more other devices using the first electrode and the second electrode, which are electrically connected to one another, and using the third electrode.

In accordance with certain embodiments, the implantable leadless biostimulator of includes a LF receiver, and a HF receiver, wherein the HF receiver is normally disabled to conserve power, wherein the LF receiver is configured to monitor for a LF wakeup pulse and in response to receiving the LF wakeup pulse enable the HF receiver so that the HF receiver can receive HF conductive communication pulses from one of the one or more other devices. The method further comprises: controlling a switch to cause the first electrode and the second electrode to be electrically disconnected from one another while the LF receiver of the implantable leadless biostimulator monitors a signal sensed between the first electrode and the third electrode for the LF wakeup pulse from one of the one or more other devices; and controlling the switch to cause the first electrode and the second electrode to be electrically connected to one another, in response to the LF receiver receiving the LF wakeup pulse and enabling the HF receiver so that the HF receiver can receive HF conductive communication pulses from the one of the one or more other devices in a signal sensed between the first electrode and the third electrode while the first electrode and the second electrode are electrically connected by the switch to one another.

In accordance with certain embodiments, the one or more other devices comprises an external device, and the method further comprises: controlling a switch to electrically connect the first electrode and the second electrode to one another while monitoring for one or more conductive communication pulses transmitted by the external device and while at least one frame is being conductively communicated between the implantable leadless biostimulator and the external device; and controlling the switch to electrically disconnect the first electrode and the second electrode from one another while not monitoring for the one or more conductive communication pulses transmitted by the external device and while no frame is being conductively communicated between the implantable leadless biostimulator and the external device.

In accordance with certain embodiments, the implantable leadless biostimulator with which the method is used is a leadless neurostimulator.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Figure 1A:
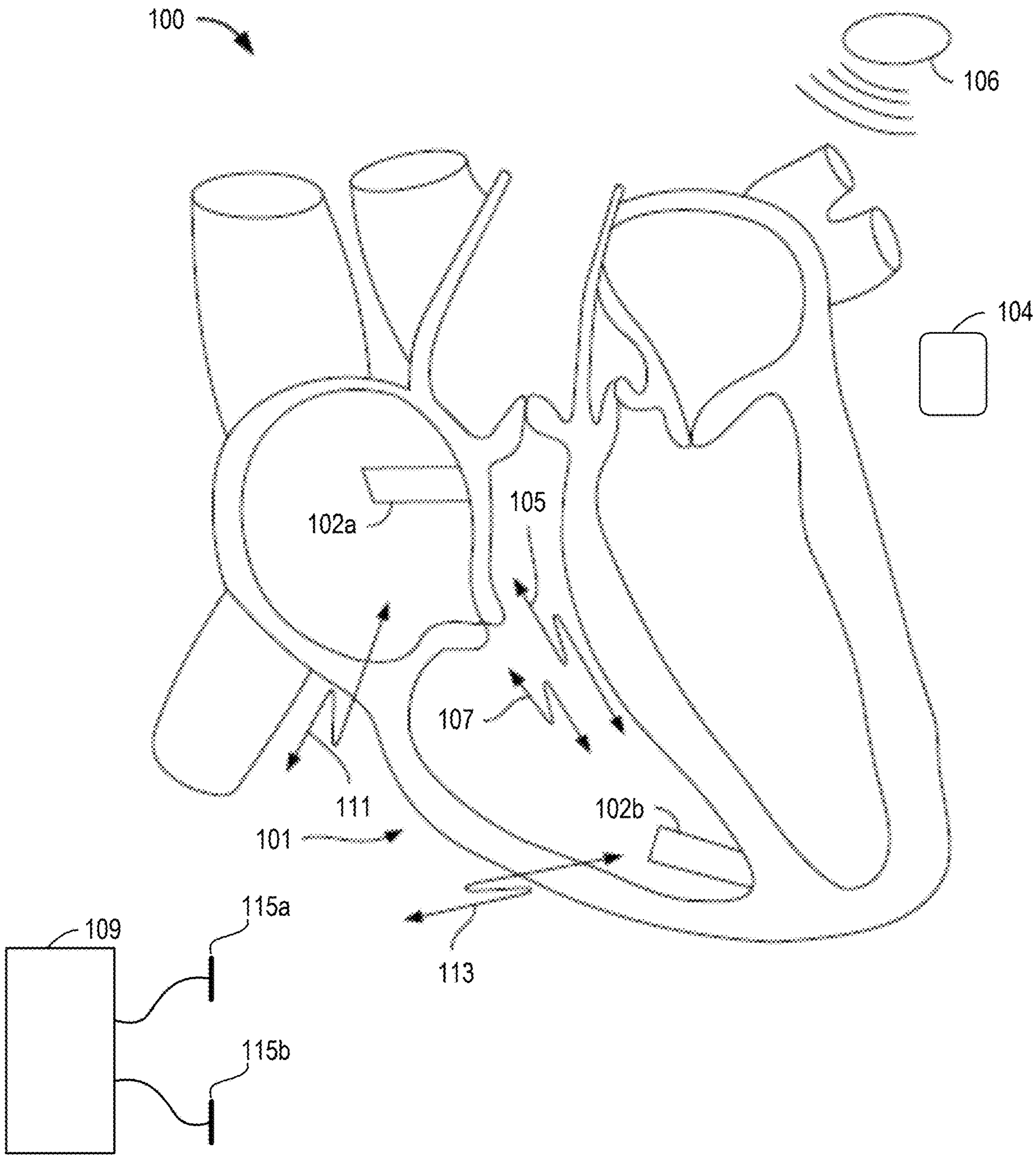
FIG. 1A illustrates a system that includes a plurality of IMDs that are implanted in a patient and an external device that can be used to program and/otherwise communicate with the IMDs.

As noted above, where an IMD is an implantable leadless biostimulator, such as, but not limited to a leadless pacemaker (LP), the implantable leadless biostimulator may use the same electrodes for performing pacing, for performing sensing of an electrocardiogram (EGM), as well as for transmitting and/or receiving conductive communication signals. More specifically, an LP may use the same pair of electrodes (e.g., a distal tip electrode and a proximal ring or can electrode) to deliver stimulation pulses for therapeutic purposes, to sense an EGM for diagnostic purposes, and to transmit and/or receive conductive communication pulses for communicative purposes. Since an LP type of implantable leadless biostimulator is quite small in size, and thus has a battery that is quite small in size, it is important to conserve as much power as possible in order to elongate battery life and thereby elongate the life of the LP.

One way to achieve elongated battery life, is to apply an insulated coating on a portion (and preferably a majority) of the distal tip electrode of the LP, in order to leave a relatively small uninsulated conductive area on the distal tip electrode to achieve higher effective impedance, as described in U.S. Patent Application Publication No. 2024/0278005 A1, titled PACING DEVICE HAVING PARTIALLY INSULATED TIP ELECTRODE, filed Feb. 7, 2024, and published Aug. 22, 2024, which is incorporated herein by reference. However, the insulated coating on the distal tip electrode reduces the transmitting signal strength of conductive communication signals. More generally, an implantable leadless biostimulator, such as a leadless pacemaker, may deliver stimulation pulses to patient tissue via a set of electrodes, e.g., a distal tip electrode and a proximal "can" or ring electrode. Overall impedance for the output pulses is based on several factors, including characteristics of the electrodes, associated electrode-to-tissue interfaces, and conductivity of tissue between electrodes. The overall impedance directly impacts the efficiency and efficacy of tissue stimulation by the implantable leadless biostimulator. Reducing the overall impedance can require more electrical current to drive stimulation (e.g., pacing), thereby draining a battery faster and reducing device longevity. Conversely, increasing overall impedance can improve device longevity, but may reduce the quality of conductive communication performed using the electrodes. An effective impedance of an electrode is influenced by an amount of exposed area of the electrode that is in contact with patient tissue. Accordingly, the effective impedance of an electrode can be controlled (e.g., to be within a specified range) by partially coating the electrode with an insulator, while leaving one or more portions of the electrode uninsulated (i.e., devoid of an insulator) and thereby exposed. Embodiments of the present technology, described herein, can be used to enhance the strength of conductive communication signals received by an LP, or other type of implantable leadless biostimulator. However, before providing addition details of the specific embodiments of the present technology, an example environment in which embodiments of the present technology can be useful will first be described with reference to FIGS. 1-3.

Figure 2A:
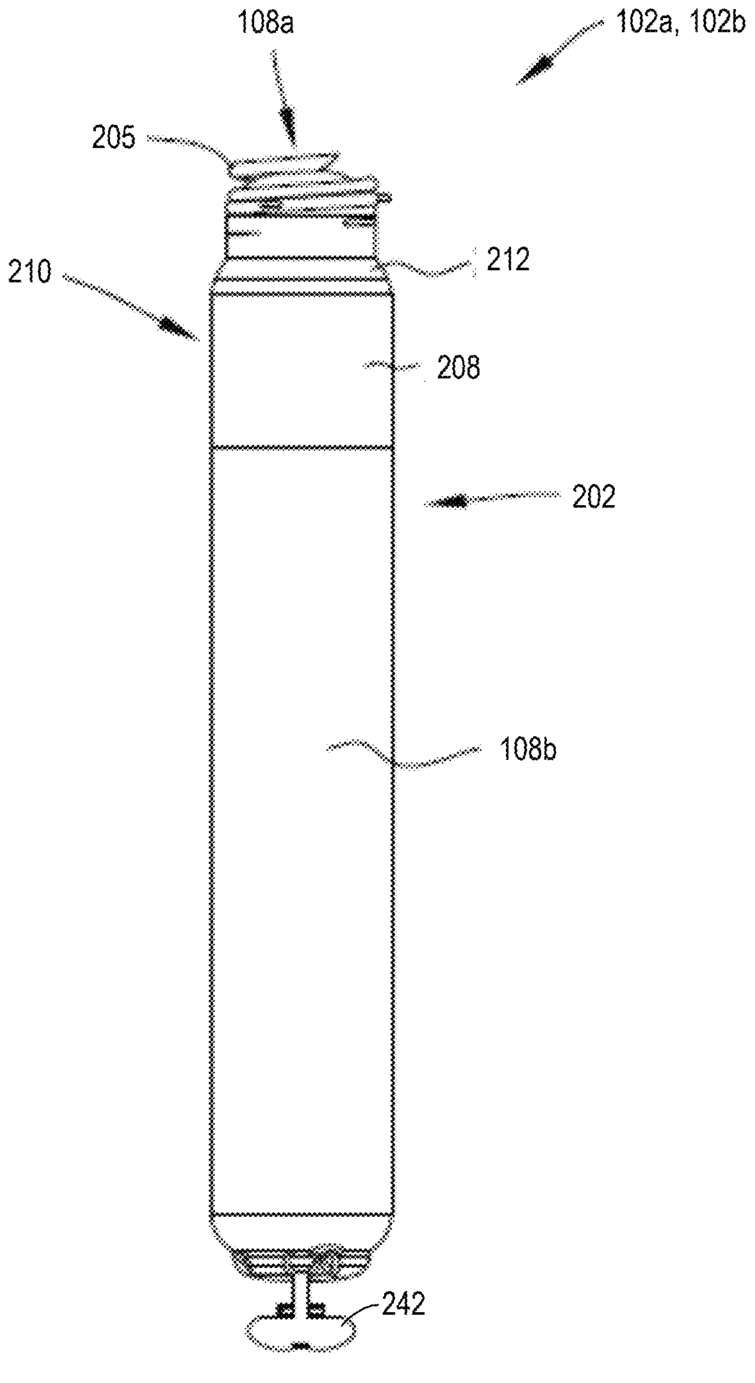
FIG. 2A illustrates an example form factor for an LP.
Figure 2B:
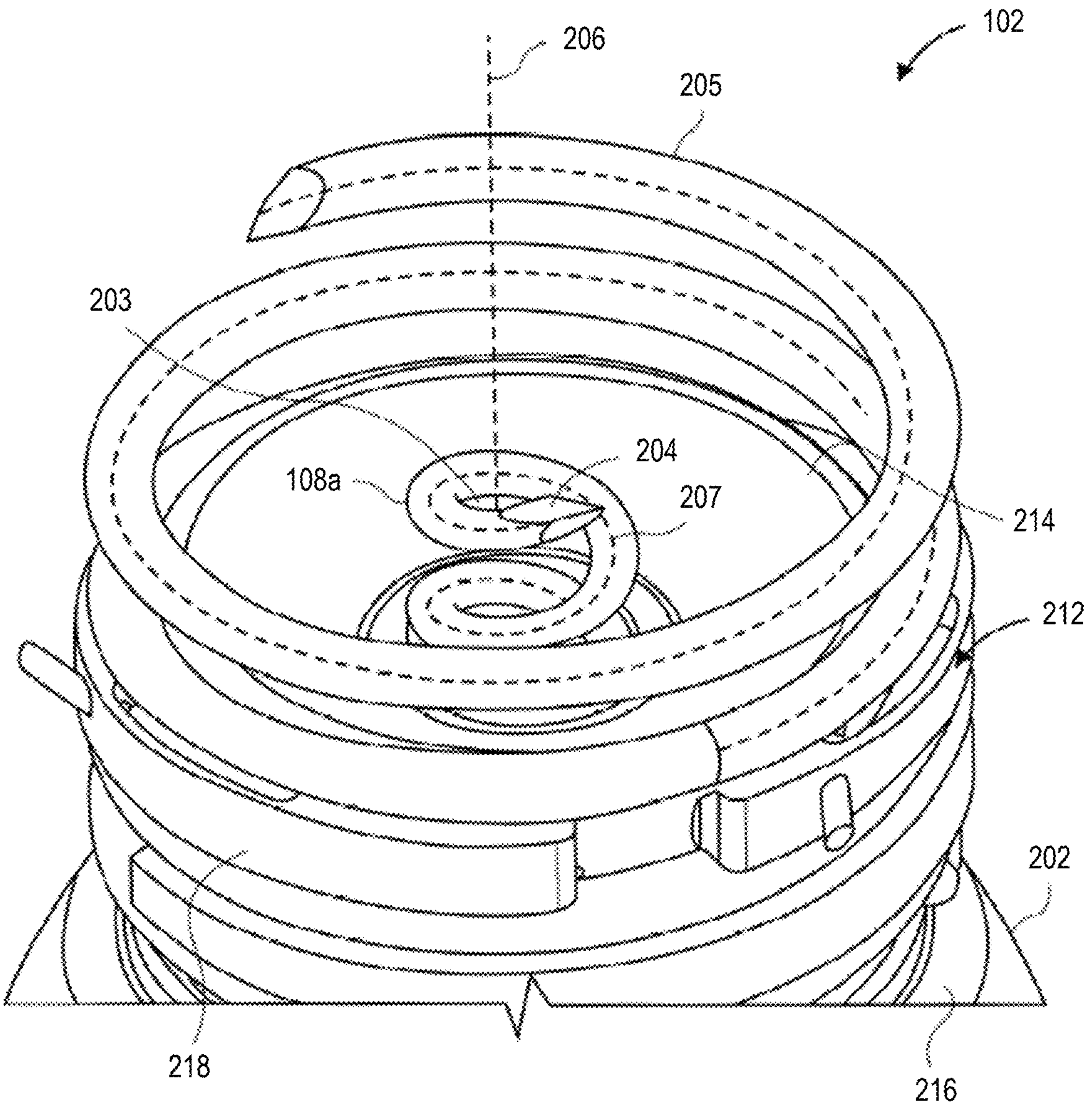
FIG. 2B is a perspective view of a distal portion of an LP having a distal tip electrode and an outer fixation element, in accordance with an embodiment.
Figure 2C:
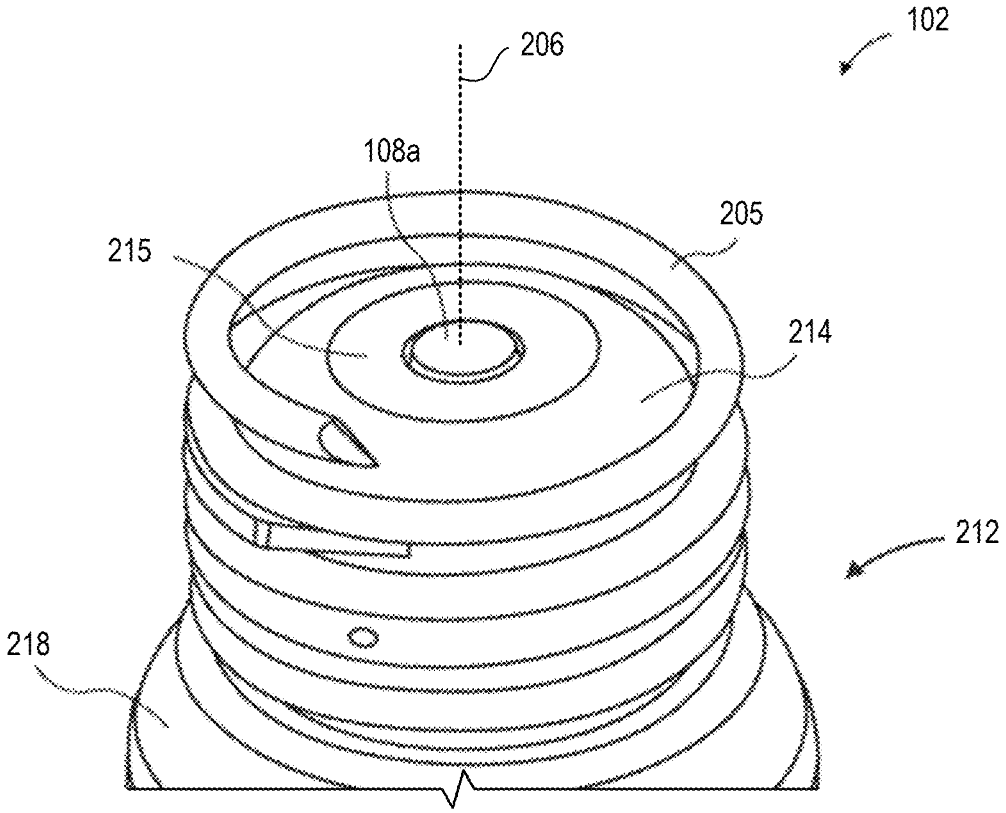
FIG. 2C is a perspective view of a distal portion of an LP having a distal tip electrode and an outer fixation element, in accordance with another embodiment.
Figure 3:
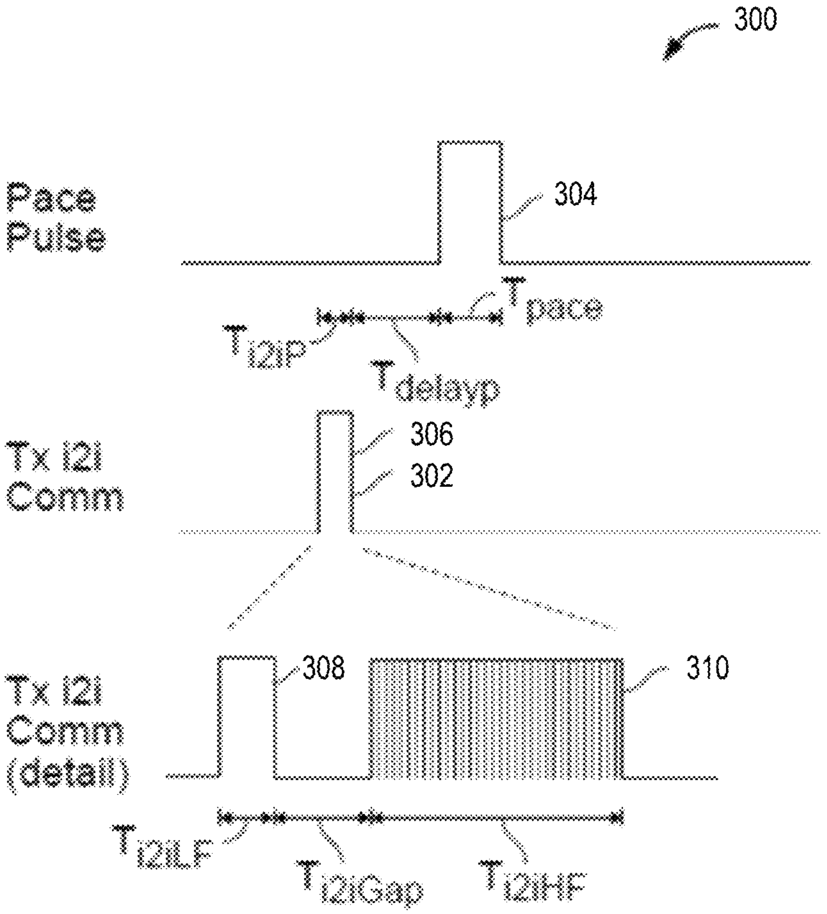
FIG. 3 is a timing diagram demonstrating one embodiment of conducted i2i communication for a paced event.

More specifically, FIGS. 1-3 will be used to describe an example cardiac pacing system, wherein pacing and sensing operations can be performed by multiple IMDs. Such systems may include one or more leadless pacemakers (LPs), an implantable cardioverter defibrillator (ICD), such as a non-vascular ICD (NV-ICD), an insertable cardiac monitor (ICM), and/or an external device. Where the system includes an ICD, the system is also capable of performing defibrillation. Where the only IMD is an ICM, the system may only be capable of performing monitoring without performing any therapy. The external device may also be referred to herein as an external medical device (EMD).

FIG. 1A illustrates a system 100 that is configured to be at least partially implanted in a heart 101. The system 100 includes LPs 102*a* and 102*b* located in different chambers of the heart 101. The LP 102*a* is located in a right atrium, while LP 102*b* is located in a right ventricle. The LPs 102*a* and 102*b* can communicate with one another to inform one another of various local physiologic activities, such as local intrinsic events, local paced events, and/or the like. The LPs 102*a* and 102*b* may be constructed in a similar manner, but operate differently based upon which chamber LP 102*a* or 102*b* is located. The LPs 102*a* and 102*b* may sometimes be referred to collectively herein as the LPs 102, or individually as an LP 102.

In certain embodiments, the LPs 102*a* and 102*b* communicate with one another, and/or with an ICM 104, and/or with an ICD 106, by conductive communication through the same electrodes that are used for sensing and/or delivery of pacing therapy. The LPs 102*a* and 102*b* also use conductive communication to communicate with a non-implanted device 109, having at least two skin electrodes 115*a* and 115*b* placed on or against the skin of a patient within which the LPs 102*a* and 102*b* are implanted. The non-implanted device 109, which can also be referred to as an external device 109, can be an external programmer that is capable of programming the LPs 102, the ICM 104, and/or the ICD 106. The external device 109 can alternatively be an external monitor, such as a bedside monitor, or a patient link monitor (PLM), that is incapable of programming the LPs 102, the ICM 104, and/or the ICD 106.

While not shown (and not preferred, since it would increase the size and power consumption of the LPs 102*a* and 102*b*), the LPs 102*a* and 102*b* can potentially include an antenna and/or telemetry coil that would enable them to communicate with one another, the ICD 106 and/or a non-implanted device using RF and/or inductive communication. While only two LPs 102 are shown in FIG. 1A, it is possible that more than two LPs can be implanted in a patient. For example, to provide for bi-ventricular pacing and/or cardiac resynchronization therapy (CRT), in addition to having LPs implanted in or on the right atrial (RA) chamber and the right ventricular (RV) chamber, a further LP can be implanted in or on the left ventricular (LV) chamber. It is also possible that a single LP be implanted within a patient, e.g., in or on the RV chamber, the RA chamber, or the LV chamber, but not limited thereto. It would also be possible for more than one LP to be implanted in or on a same cardiac chamber.

In some embodiments, one or more of the LPs 102*a*, 102*b* can be co-implanted with the ICM 104 and/or the ICD 106. In such embodiments, the ICM 104 and/or the ICD 106 are examples of other types of IMDs that may need to communicate with an external device, such as an external programmer, from time to time. The ICM 104 and/or the ICD 106 may utilize conductive communication to communicate with the LPs 102, as well as to communicate with an external device. It may alternatively or additionally be possible for the ICM 104 and/or the ICD 106 to utilize radio frequency (RF) communication and/or inductive communication to communicate with an external device, depending upon the specific implementation, and depending upon the capabilities of the external device.

Each LP 102 uses two or more electrodes located within, on, or within a few centimeters of the housing of the LP 102, for pacing and sensing at the cardiac chamber, for bidirectional conductive communication with one another, with the external device 109, the ICD 106, and/or the ICM 104. Such an ICM 104 can be intended for subcutaneous implantation at a site near the heart 101. The ICM 104 can include, for example, a pair of spaced-apart sense electrodes positioned with respect to a housing, wherein the sense electrodes provide for detection of far-field EGM signals, and can also be used for conductive communication with one or more other implanted devices, such as the LP(s) 102*a* and/or 102*b* and/or the ICD 106, and/or can be used for conductive communication with the external device 109. Such an ICM 104 can also include an antenna that is configured to wirelessly communicate with an external device using one or more wireless communication protocols (e.g., Bluetooth, Bluetooth low energy, Wi-Fi, etc.). The housing of the ICM 104 can include various other components such as: sense electronics for receiving signals from the electrodes, a microprocessor for processing the signals in accordance with algorithms, a loop memory for temporary storage of cardiac activity (CA) data, a device memory for long-term storage of CA data upon certain triggering events, sensors for detecting patient activity and a battery for powering components.

Each LP 102 and/or other type of IMD 104, 106 can transmit an advertisement sequence using at least two electrodes of the IMD 104, 106 (e.g., LP 102) from time to time so that an external device 109 (e.g., an external programmer, or a remote monitor) that has or is communicatively coupled to external electrodes that are in contact with the patient (within which the LP(s) 102 and/or other IMD(s) 104, 106 is/are implanted) can detect the presence of the IMD(s) 104, 106 (e.g., LP 102) and optionally establish an active conductive telemetry session (which can also be referred to as an active conductive communication session) with one or more IMD(s) 104, 106 (e.g., LP 102). For a more specific example, an LP 102 (or other type of IMD 104, 106) can transmit an advertisement sequence once every specified number of cardiac cycles (e.g., once every eight cardiac cycles), or once every specified period of time (e.g., once every 5 seconds), but is not limited thereto. In certain embodiments, the external device 109 can use the advertisement sequence to initiate an active conductive telemetry session (aka an active conductive communication session) with an LP 102 (or another type of IMD 104, 106), as will be described in additional detail below.

Figure 1B:
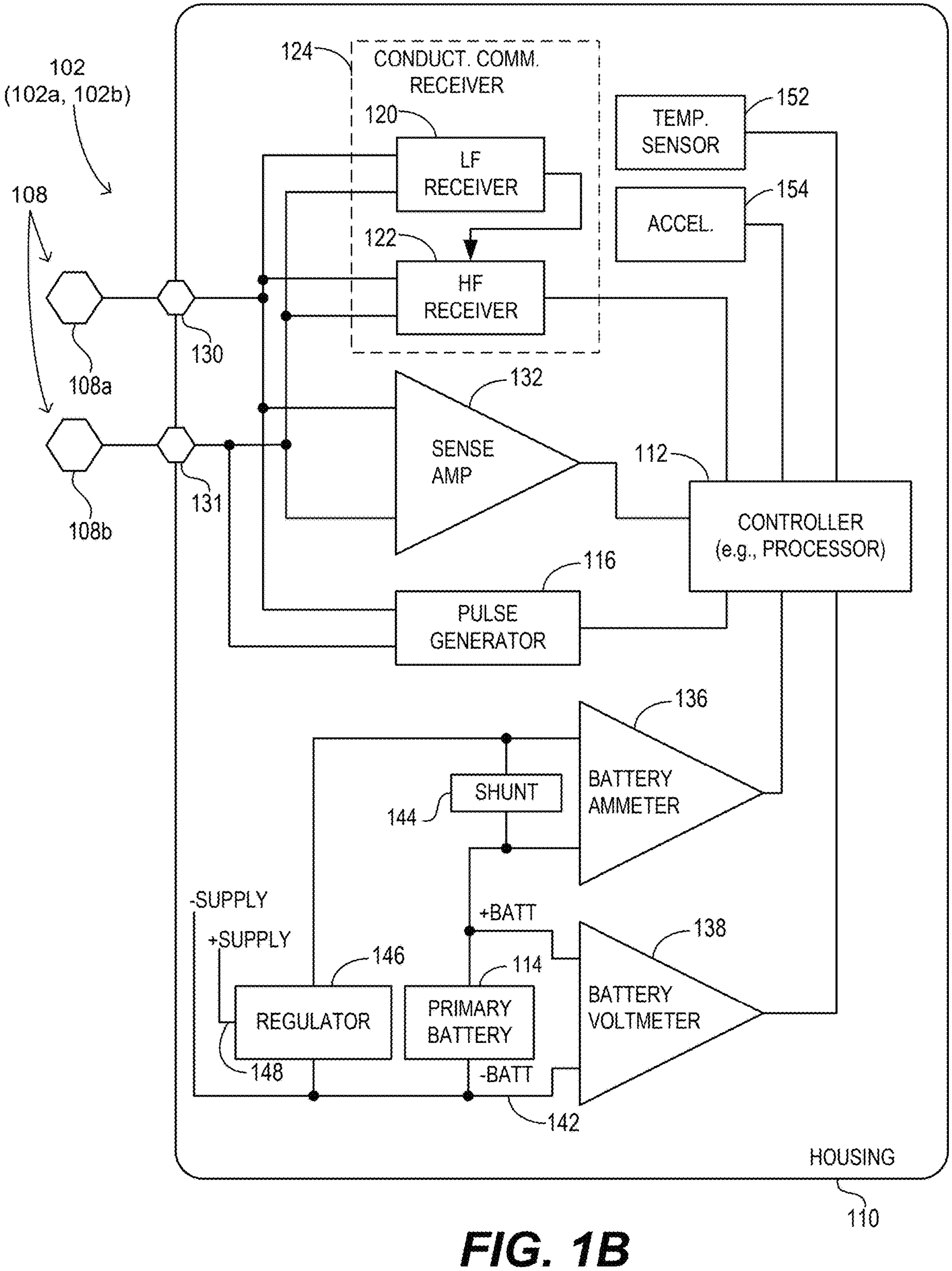
FIG. 1B is a high level block diagram of an example LP.

Referring to FIG. 1B, a block diagram shows an example embodiment for portions of the electronics within the LPs 102*a*, 102*b* configured to provide conductive communication through the same electrodes that are used for cardiac pacing and/or sensing. Each of the LPs 102*a*, 102*b* includes at least two leadless electrodes configured for delivering cardiac pacing pulses, sensing evoked and/or natural cardiac electrical signals, and uni-directional and/or bi-directional communication. In FIG. 1B (and FIG. 2A) the two electrodes shown therein are labeled 108*a* and 108*b*. Such electrodes can be referred to collectively as the electrodes 108, or individually as an electrode 108. An LP 102, or other type of IMD, can include more than two electrodes, depending upon implementation. In certain embodiments, the electrode 108*b* is provided by at least a portion of an electrically conductive housing 110. As will be described in additional detail below, e.g., initially with reference to FIGS. 2B and 2C, in certain embodiments one or more of the LPs 102 can also include one or more additional electrodes, e.g., such as the electrode 205 (shown in and initially discussed with reference to FIG. 2B) or the electrode 215 (shown in and initially discussed with reference to FIG. 2C).

In FIG. 1B, each of the LPs 102*a*, 102*b* is shown as including first and second receivers 120 and 122 that collectively define separate first and second communication channels 105 and 107 (FIG. 1A), (among other things) between LPs 102*a* and 102*b*. Although first and second receivers 120 and 122 are depicted, in other embodiments, LP 102*a*, 102*b* may only include one receiver 120 or 122, or may include additional receivers other than first and second receivers 120 and 122. The receivers 120 and 122 can also be referred to, respectively, as a low frequency (LF) receiver 120 and a high frequency (HF) receiver 122, because the receiver 120 is configured to monitor for one or more signals within a relatively low frequency range (e.g., below 100 kHz, or below 250 kHz) and the receiver 122 is configured to monitor for one or more signals within a relatively high frequency range (e.g., above 100 kHz, or above 250 kHz). In certain embodiments, the receiver 120 (and more specifically, at least a portion thereof) is always enabled and monitoring for a wakeup notice, which can simply be a wakeup pulse, within a specific low frequency range (e.g., between 1 kHz and 100 kHz, or between 1 kHz and 250 kHz); and the receiver 122 is selectively enabled by the receiver 120. The receiver 120 is configured to consume less power than the receiver 122 when both the first and second receivers are enabled. Accordingly, the receiver 120 can also be referred to as a low power receiver 120, and the receiver 122 can also be referred to as a high power receiver 122. The low power receiver 120 is incapable of receiving signals within the relatively high frequency range (e.g., above 100 kHz, or above 250 kHz), but consumes significantly less power than the high power receiver 122. This way the low power receiver 120 is capable of always monitoring for a wakeup notice without significantly depleting the battery (e.g., primary battery 114) of the LP 102. In accordance with certain embodiments, the high power receiver 122 is selectively enabled by the low power receiver 120, in response to the low power receiver 120 receiving a wakeup notice, so that the high power receiver 122 can receive the higher frequency signals, and thereby handle higher data throughput needed for effective i2i (or e2i) communication without unnecessarily and rapidly depleting the battery 114 of the LP 120 (which the high power receiver 122 may do if it were always enabled). Since the receivers 120, 122 are used to receive conducted communication messages, the receivers 120, 122 can be collectively, or individually, be referred to as a conductive communication receiver 124. In certain embodiments, the LP 102 includes only a single conducted communication receiver. An example of a single conducted communication receiver, which can be included in the LPs and/or other types of IMDs referred to herein, is described in commonly assigned U.S. Pat. No. 12,113,649, titled "Fully-Differential Receiver for Receiving Conducted Communication Signals," issued Oct. 8, 2024.

Optionally, an LP (or other IMD) that receives any conductive communication signal from another LP (or other IMD) or from a non-implanted device (aka an external device) may transmit a receive acknowledgement indicating that the receiving LP (or other IMD, or external device) received the conductive communication signal. In certain embodiments, where an IMD expects to receive a conductive communication signal within a window, and fails to receive the conductive communication signal within the window, the IMD may transmit a failure-to-receive acknowledgement indicating that the receiving IMD failed to receive the conductive communication signal. Other variations are also possible and within the scope of the embodiments described herein. Each conductive communication signal can include one or more sequences of conductive communication pulses. In accordance with certain embodiments, conductive communication pulses are delivered during cardiac refractory periods that are identified or detected by the LP(s) and/or other IMD(s). In accordance with certain embodiments, conductive communication pulses are sub-threshold, i.e., they are below the capture threshold for the patient.

The LPs 102*a*, 102*b* can exchange event messages within i2i conductive communication signals to enable synchronized therapy and additional supportive features (e.g., measurements, etc.). To maintain synchronous therapy, each of the LPs 102*a*, 102*b* is made aware (through the event messages) when an event occurs in the chamber containing the other LP 102*a*, 102*b*.

For synchronous event signaling, LPs 102*a* and 102*b* may maintain synchronization and regularly communicate at a specific interval. Synchronous event signaling allows the transmitter and receiver in each LP 102*a*, 102*b* to use limited (or minimal) power as each LP 102*a*, 102*b* is only powered for a small fraction of the time in connection with transmission and reception. For example, LP 102*a*, 102*b* may transmit/receive (Tx/Rx) communication messages in time slots having duration of 10-20 μs, where the Tx/Rx time slots occur periodically (e.g., every 10-20 ms). Such time slots can also be referred to as windows.

Still referring to FIG. 1B, each LP 102*a*, 102*b* is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102*a*, 102*b* is located, such as when the associated chamber is not in a refractory state. In addition, an LP 102*a*, 102*b* that receives an event message may enter an "event refractory" state (or event blanking state) following receipt of the event message. The event refractory/blanking state may be set to extend for a determined period of time after receipt of an event message in order to avoid the receiving LP 102 from inadvertently sensing another signal as an event message that might otherwise cause retriggering. For example, the receiving LP 102 may detect a measurement pulse from another LP 102 or the external device 109.

In accordance with certain embodiments herein, the external device 109 may communicate over an external device-to-LP channel (e.g., 111, 113 in FIG. 1A), with LPs 102*a*, 102*b* utilizing the same communication scheme. The external device 109 may listen to the event message transmitted between LPs 102*a*, 102*b* and synchronize external device to implant communication such that the external device 109 does not transmit communication signals 113 until after an implant to implant messaging sequence is completed.

In some embodiments, an individual LP 102 can comprise a hermetic housing 110 configured for placement on or attachment to the inside or outside of a cardiac chamber and at least two leadless electrodes 108 proximal to the housing 110 and configured for conductive communication with at least one other device within or outside the body. Depending upon the specific implementation, and/or the other device with which an LP 102 is communicating, the conductive communication may be unidirectional or bidirectional.

FIG. 1B shows functional elements of the LP 102 substantially enclosed in a hermetic housing 110. The LP 102 has at least two electrodes 108*a*, 108*b* located within, on, or near the housing 110, for delivering pacing pulses to and sensing electrical activity from the muscle of the cardiac chamber, and for conductive communication with at least one other device within or outside the body. The electrodes 108*a*, 108*b* can be referred to collectively as the electrodes 108, or individually as an electrode 108, as noted above. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receiver 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example an optional battery current monitor 136 and an optional battery voltage monitor 138, and can contain circuits for controlling operations in a predetermined manner. As will be described in additional detail further below, the LP 102 can include other electrodes in addition to the electrodes 108*a*, 108*b*.

The electrodes 108 can be configured to communicate bidirectionally among the multiple leadless cardiac pacemakers, the implanted ICD 106 and/or the implanted ICM 104 to coordinate pacing pulse delivery and optionally other therapeutic or diagnostic features using messages that identify an event at an individual pacemaker originating the message and a pacemaker receiving the message react as directed by the message depending on the origin of the message. An LP 102*a*, 102*b* that receives the event message reacts as directed by the event message depending on the message origin or location. In some embodiments or conditions, the two or more leadless electrodes 108 can be configured to communicate bidirectionally among the one or more LPs, the ICD 106, and/or the ICM 104 and transmit data including designated codes for events detected or created by an individual pacemaker. Individual pacemakers can be configured to issue a unique code corresponding to an event type and a location of the sending pacemaker. The electrodes 108 can also be used to transmit and/or receive conductive communication signals to/from the external device 109.

Also shown in FIG. 1B, the primary battery 114 has positive terminal 140 and negative terminal 142. Current from the positive terminal 140 of primary battery 114 flows through an optional shunt 144 to an optional regulator circuit 146 to create a positive voltage supply 148 suitable for powering the remaining circuitry of the LP 102. The optional shunt 144 enables the optional battery current monitor 136 to provide the controller 112 with an indication of battery current drain and indirectly of device health. The illustrative power supply can be the primary battery 114.

The LP 102*a*, 102*b* is also shown as including an optional temperature sensor 152 and an optional accelerometer 154, which may be used to control rate responsive pacing, but may include just one of those, but not the other. The optional temperature sensor 152 can be any one of various types of well-known temperature sensors, or can be a future developed temperature sensor. The optional temperature sensor 152 and/or the optional accelerometer 154 can be used in various manners. For example, the optional temperature sensor 152 and/or the optional accelerometer 154 can be used to detect an activity level of the patient to adjust a pacing rate, i.e., for use in rate responsive pacing. When a person starts to exercise their core body temperature initially dips, and then after exercising for a prolonged period of time the person's core body temperature will eventually rise. Thereafter, when the person stops exercising their core body temperature will return to its baseline. Accordingly, the controller 112 can be configured to detect an activity level of a patient based on core blood temperature measurements obtained using the optional temperature sensor 152.

In various embodiments, each LP 102*a*, 102*b* can manage power consumption to draw limited power from the battery 114, thereby reducing device volume. Each circuit in the LP 102 can be designed to avoid large peak currents. For example, cardiac pacing can be achieved by discharging a tank capacitor (not shown) across the pacing electrodes 108. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 can access signals on the electrodes 108 and can examine output pulse amplitude, duration, etc. from another LP for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

FIG. 2A shows an example form factor of an LP 102*a*, 102*b*. The LP 102*a*, 102*b* can include a hermetic housing 202 (corresponds to housing 110 in FIG. 1B) with electrodes 108*a* and 108*b* disposed thereon. As shown, electrode 108*a* can be separated from but surrounded partially by a fixation element 205, and the electrode 108*b* can be disposed on the housing 202. The fixation element 205 can be a fixation helix, a plurality of hooks, barbs, or other attaching features configured to attach the pacemaker to tissue, such as heart tissue. The electrodes 108*a* and 108*b* are examples of the electrodes 108 shown in and described above with reference to FIG. 1B. The housing 202 can also include an electronics compartment 210 within the housing 202 that contains the electronic components for operation of the LP 102*a*, 102*b*, including, e.g., a pulse generator, receiver(s), a battery, and a controller (e.g., processor) for operation. The hermetic housing 202 can be adapted to be implanted on or in a human heart, and can be cylindrically shaped, rectangular, spherical, or any other appropriate shapes, for example. The housing 202 can comprise a conductive, biocompatible, inert, and anodically safe material such as titanium, 316L stainless steel, or other similar materials. The housing 202 can further comprise an insulator disposed on the conductive material to separate electrodes 108*a* and 108*b*. The insulator can be an insulative coating on a portion of the housing 202 between the electrodes 108*a* and 108*b*, and can comprise materials such as silicone, polyurethane, parylene, or another biocompatible electrical insulator commonly used for implantable medical devices. In the embodiment of FIG. 2A, a single insulator 208 is disposed along the portion of the housing 202 between electrodes 108*a* and 108*b*. In some embodiments, the housing 202 itself can comprise an insulator instead of a conductor, such as an alumina ceramic or other similar materials, and the electrodes can be disposed upon the housing. The LP 102 is shown as including a retrieval feature 242, which can include a "button" or circular grasping feature that is configured to dock within a docking cap or a retrieval catheter that can be used to remove the LP 102 when it needs to be removed and/or replaced.

As shown in FIG. 2A, the LP 102*a*, 102*b* can further include a header assembly 212 to isolate the electrodes 108*a* and 108*b* from one another. The header assembly 212 can be made from PEEK, tecothane or another biocompatible plastic, and can contain a ceramic to metal feedthrough, a glass to metal feedthrough, or other appropriate feedthrough insulator as known in the art. The term metal, as used herein, also encompasses alloys that are electrically conductive. The electrodes 108*a* and 108*b* can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2A, electrode 108*a* can be a pace/sense electrode and electrode 108*b* can be a return electrode. The electrode 108*b* can be a portion of the conductive housing 202 that does not include the insulator 208.

Since the electrode 108*a* is shown as being located on a tip of the LP 102 at a distal end of the LP 102, the electrode 108*a* can also be referred to herein as a tip electrode, a distal electrode, or a distal tip electrode. Since the electrode 108*b* is shown as being located on a proximal portion of the LP 102, the electrode 108*b* can also be referred to herein as a proximal electrode. Where the electrode 108*b* is provided by a portion of the conductive housing 202 of the LP 102, the electrode may also be referred to herein as a "can" electrode, or a proximal "can" electrode.

Several techniques and structures can be used for attaching the housing 202 to the interior or exterior wall of the heart. A helical fixation element 205, can enable insertion of the device endocardially or epicardially through a guiding catheter. A torqueable catheter can be used to rotate the housing 202 and force the fixation element 205 into heart tissue, thus affixing the fixation element 205 (and also the electrode 108*a* in FIG. 1B) into contact with stimulable tissue. The electrode 108*b* can serve as an indifferent or return electrode for sensing and pacing. The fixation element 205 may be coated partially or in full for electrical insulation, and a steroid-eluting matrix may be included on or near the device to minimize fibrotic reaction, as is known in conventional pacing electrode-leads.

FIG. 2B is a perspective view of a distal portion of the LP 102, according to certain embodiments. Referring to FIG. 2B, the distal portion of the LP 102 is shown as having a distal tip electrode 108*a* and an outer fixation element 205. In the embodiment shown, the distal tip electrode 108*a* is coaxially arranged with the outer fixation element 205 about a longitudinal axis 206 of the LP 102. More particularly, the distal tip electrode 108*a* can extend helically about the longitudinal axis 206 at a location that is radially inward from the outer fixation element 205. The outer fixation element 205 may therefore be coupled to the housing 202 radially outward of the distal tip electrode 108*a*. The distal tip electrode 108*a* can extend along a spiral axis 207 about the longitudinal axis 206. The helical configuration of the distal tip electrode 108*a* can define an inner lumen 203. More particularly, an inner lumen 203 can pass through the distal tip electrode 108*a* along the longitudinal axis 206. The inner lumen 203 is a space surrounded by the helical electrode 108*a*, which may be exposed to a surrounding environment laterally through gaps between turns of the spiraling distal tip electrode 108*a*. The distal tip electrode 108*a* can extend distally to an electrode tip 204. The electrode tip 204 may be longitudinally proximal to, distal to, or coincident with a distal tip of the outer fixation element 205. The distal tip electrode 108*a* can be a helical element to screw into target tissue. Accordingly, when the outer fixation element 205 screws into the tissue, the tip electrode 108*a* can also engage the target tissue, and the housing 202 can be rotated to cause the electrode tip 204 of the distal tip electrode 108*a* to pierce the tissue and anchor the LP 102.

The distal tip electrode 108*a* can be an active electrode, and can electrically communicate with the pacing circuitry contained in the electronics compartment 210. Accordingly, the anchored distal tip electrode 108*a* can electrically communicate with the tissue, and can transmit electrical pulses between the tissue and the pacing circuitry of the LP 102. To facilitate electrical function of the distal tip electrode 108*a*, and as described further below, the distal tip electrode 108*a* may be coated in titanium nitride, iridium oxide, platinum black, etc. to reduce a polarization value of the distal tip electrode 108*a*. By way of example, the titanium nitride coating may be in a range of 5 to 50 microns, e.g., 13 microns. The polarization value of the distal tip electrode 108*a* may similarly be reduced by etching a surface of the distal tip electrode using chemical or laser treatment.

In an embodiment, the LP 102 includes the header assembly 212. The header assembly 212 includes the outer fixation element 205 mounted on a helix mount 214. The helix mount 214 includes features that interact with the housing 202 and/or a flange 216, the outer fixation element 205, and the target tissue. In an embodiment, the helix mount 214 includes a helix mount flange 218. The helix mount flange 218 can act as a mounting thread that extends around the longitudinal axis 206. A mounting thread structure of the helix mount flange 218 can be helical such that spiraling turns of the helix mount flange 218 are separated by helix mount gaps that also spiral about the longitudinal axis 206. The outer fixation element 205 can be received within the threaded groove (the helix mount gaps) of helix mount 214 as shown in FIG. 2B. For example, an assembler can insert a proximal end of the outer fixation element 205 into a distal end of the helical gap and rotate the outer fixation element 205 relative to the helix mount 214 to cause the helical fixation element to advance along and thread onto the helix mount 214.

As noted above, the distal tip electrode 108*a* can also be referred to as a distal tip electrode, or as a distal electrode, since it is located on a distal portion of the LP 102. In alternative embodiments, the distal tip electrode 108*a* can be a button electrode that is not helical, but is not limited thereto. It is also noted that in alternative embodiments, the fixation element 205 need not be helical, but rather, can have other shapes that provide for fixation, such as one or more tines or barbs, but not limited thereto.

FIG. 2C is a perspective view of a distal portion of an LP 102 having a distal tip electrode 108*a* and an outer fixation element 205, in accordance with another embodiment. Components in FIG. 2C that are the same or similar to those in FIG. 2B are labeled the same. Referring to FIG. 2C, the distal portion of the LP 102 is shown as having a distal tip electrode 108*a* and an outer fixation element 205. In the embodiment shown in FIG. 2C, the distal tip electrode 108*a* is coaxially arranged with the outer fixation element 205 about a longitudinal axis 206 of the LP 102. In contrast to the embodiment of FIG. 2B, in FIG. 2C the distal tip electrode 108*a* is a button electrode, rather than a helical electrode as was the case in FIG. 2B. The outer fixation element 205 is coupled to the housing 202 radially outward of the distal tip electrode 108*a*. When the outer fixation element 205 screws into the tissue, the tip electrode 108*a* can also engage the target tissue, but without piercing the target tissue, in contrast to the embodiment of FIG. 2B. The distal tip electrode 108*a* can be an active electrode, and can electrically communicate with the pacing circuitry contained in the electronics compartment 210. Accordingly, the anchored distal tip electrode 108*a* can electrically communicate with the tissue, and can transmit electrical pulses between the tissue and the pacing (or other stimulation) circuitry of the LP 102. As was also the case in the embodiment described above with reference to FIG. 2B, the distal tip electrode 108*a* may be coated in titanium nitride, iridium oxide, platinum black, etc. to reduce a polarization value of the distal tip electrode 108*a*. FIG. 2C also shows an electrically conductive distal ring 215 that surrounds the distal tip electrode 108*a*, and is physically separate from the distal tip electrode 108*a*. Additional details of how electrically conductive distal ring 215, which can also be referred to herein an a distal ring electrode 215, may be used are discussed below in the discussion of FIGS. 5A-5D.

In accordance with certain embodiments of the present technology, the fixation element 205 is made entirely, or at least partially, of an electrically conductive material, and the fixation element 205 is used as an electrode to transmit and/or receive conductive communication pulses. Accordingly, in such embodiments, the fixation element 205 can be referred to as an electrode. Alternatively, or additionally, the electrically conductive distal ring 215 is used as an electrode to transmit and/or receive conductive communication pulses. Accordingly, in such embodiments, the electrically conductive distal ring 215 can be referred to as an electrode.

When discussing FIGS. 1A-2C, each of the LPs 102 was shown and described as including only one proximal electrode. In alternative embodiments, one or more of the LPs 102 can include more than one proximal electrode, e.g., two proximal electrodes. Examples of an LP that includes at least two proximal electrodes are described with reference to FIGS. 9A and 9B of commonly assigned U.S. Pat. No. 10,642,705. For a specific example, at least a portion of the retrieval feature 242 (FIG. 2A) is made of an electrically conductive material and is used as a proximal electrode.

FIG. 3 is a timing diagram 300 demonstrating one example of a conducted i2i communication for a paced event. The i2i communication may be transmitted, for example, from LP 102*a* to LP 102*b*. As shown in FIG. 3, in this embodiment, an i2i transmission 302 is sent prior to delivery of a pace pulse 304 by the transmitting LP (e.g., LP 102*a*). This enables the receiving LP (e.g., LP 102*b*) to prepare for the remote delivery of the pace pulse. The i2i transmission 302 includes an envelope 306 that may include one or more individual pulses. For example, in this embodiment, envelope 306 includes a low frequency pulse 308 (e.g., a wakeup pulse) followed by a high frequency pulse train 310. Low frequency pulse 308 lasts for a period $T_{i2iLF}$, and high frequency pulse train 310 lasts for a period $T_{i2iHF}$. The end of low frequency pulse 308 and the beginning of high frequency pulse train 310 are separated by a gap period, $T_{i2iGap}$.

As shown in FIG. 3, the i2i transmission 302 lasts for a period $T_{i2ip}$, and pace pulse 304 lasts for a period Tpace. The end of i2i transmission 302 and the beginning of pace pulse 304 are separated by a delay period, $T_{delayp}$. The delay period may be, for example, between approximately 0.0 and 10.0 milliseconds (msec), particularly between approximately 0.1 msec and 2.0 msec, and more particularly approximately 1.0 msec. The terms approximately and about, as used herein, mean +/−10% of a specified value.

Figure 4:
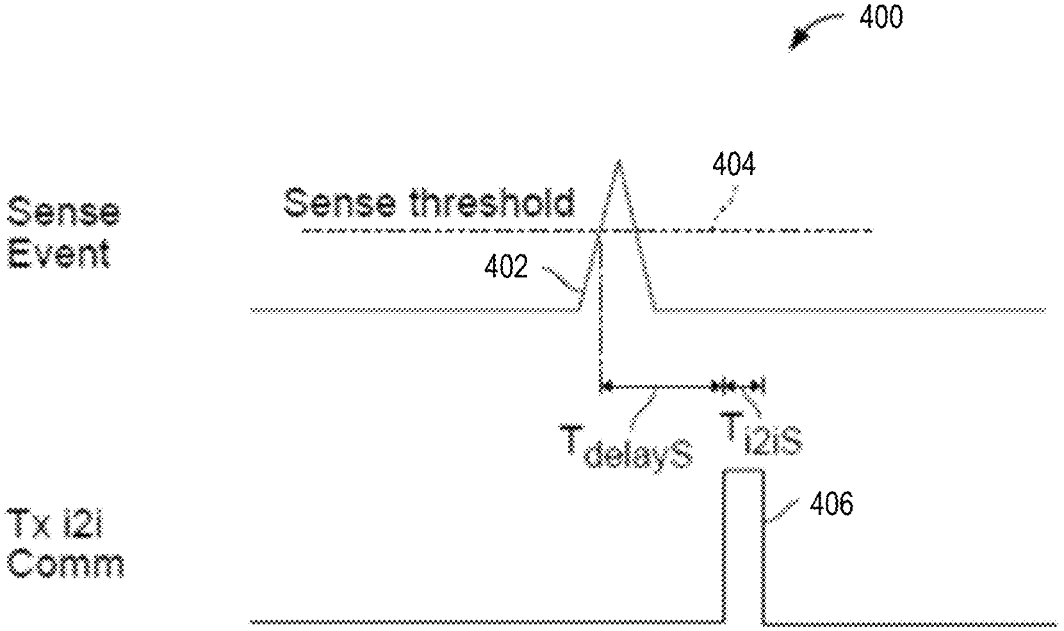
FIG. 4 is a timing diagram demonstrating one embodiment of conducted i2i communication for a sensed event.

FIG. 4 is a timing diagram 400 demonstrating one example of a conducted i2i communication for a sensed event. The i2i communication may be transmitted, for example, from LP 102*a* to LP 102*b*. As shown in FIG. 4, in this embodiment, the transmitting LP (e.g., LP 102*a*) detects the sensed event when a sensed intrinsic activation 402 crosses a sense threshold 404. A predetermined delay period, $T_{delayS}$, after the detection, the transmitting LP transmits an i2i transmission 406 that lasts a predetermined period $T_{i2iS}$. The delay period may be, for example, between approximately 0.0 and 10.0 milliseconds (msec), particularly between approximately 0.1 msec and 2.0 msec, and more particularly approximately 1.0 msec.

As with i2i transmission 302, i2i transmission 406 may include an envelope that may include one or more individual pulses. For example, similar to envelope 306, the envelope of i2i transmission 406 may include a low frequency pulse followed by a high frequency pulse train. In accordance with certain embodiments, the duration of each of the periods $T_{i2ip}$ and $T_{i2iS}$ can be in the range of 1.5 msec to 13 msec, and more preferably, be within the range of 2.0 msec to 5.0 msec. This duration includes the both the low frequency pulse (e.g., 308) and the high frequency pulse train (e.g., 310, that follows the low frequency pulse). The low frequency pulse (e.g., 308) can be used as a wakeup pulse, and the high frequency pulse train (e.g., 310, that follows the low frequency pulse) can be used as a communication event marker and payload.

As noted above, an implantable leadless biostimulator, such as an LP 102, is quite small in size, and thus has a battery (e.g., primary battery 114 in FIG. 1B) that is quite small in size. Accordingly, it is important to conserve as much power as possible in order to elongate battery life and thereby elongate the life of the implantable leadless biostimulator. As noted above, one way to achieve elongated battery life is to apply an insulated coating on a portion (and preferably a majority) of the distal tip electrode 108*a* of the implantable leadless biostimulator, in order to leave a relatively small uninsulated conductive area on the distal tip electrode 108*a* to achieve higher effective impedance, as described in U.S. Patent Application Publication No. 2024/0278005 A1, titled PACING DEVICE HAVING PARTIALLY INSULATED TIP ELECTRODE, filed Feb. 7, 2024, and published Aug. 22, 2024, which has been incorporated herein by reference. However, the insulated coating on the distal tip electrode 108*a* reduces the transmitting signal strength of conductive communication signals that are transmitted and received using the distal tip electrode 108*a* and the proximal electrode 108*b* of the LP 102, which may result in poor conductive communication quality. Embodiments of the present technology, described herein, can be used to enhance the strength of conductive communication signals received and transmitted by the LP 102, or other type of implantable leadless biostimulator, to thereby improve the conductive communication quality, as will now be described below.

In accordance with certain embodiments of the present technology, the fixation element 205 is made entirely, or at least partially, of an electrically conductive material such that a portion of the fixation element 205 that is in contact with patient tissue (e.g., cardiac tissue, but not limited thereto) has a larger electrically conductive surface area in contact with patient tissue than does the distal tip electrode 108*a*, wherein the distal tip electrode 108*a*, as noted above, may be partially coated with an insulator to improve battery longevity. In other words, an electrically conductive surface area of the fixation element 205 that is in physical contact with patient tissue is greater than an electrically conductive surface area of the distal tip electrode 108*a* that is in physical contact with the patient tissue. In certain such embodiments, the larger electrically conductive surface area of the fixation element 205 is advantageous used to improve conductive communication by using the fixation element 205 as one of the electrodes that is used for transmitting and/or receiving conductive communication pulses. Since the fixation element 205 in such embodiments functions as a conductive communication electrode, the fixation element 205 is often referred to herein as an electrode, or as one of a plurality or set of electrodes.

As described in more detail below, there are various different ways that the larger electrically conductive surface area of the fixation element 205 can be used to improve conductive communication quality. Also, as will be described in additional detail below, other types of electrically conductive elements (aka electrodes) besides the fixation element 205 (or in additional to the fixation element 205) can be used to improve conductive communication, so long as those other types of electrically conductive elements (aka electrodes) have an electrically conductive surface area in physical contact with patient tissue that is greater than an electrically conductive surface area of the distal tip electrode 108*a* that is in physical contact with the patient tissue. For example, an electrically conductive distal ring 215 (shown in FIG. 2C) that surrounds the distal tip electrode 108*a* and is physically separate from the distal tip electrode 108*a*, can be used to improve conductive communication if the electrically conductive distal ring 215 has an electrically conductive surface area in physical contact with patient tissue that is greater than an electrically conductive surface area of the distal tip electrode 108*a* that is in physical contact with the patient tissue.

Figure 5A:
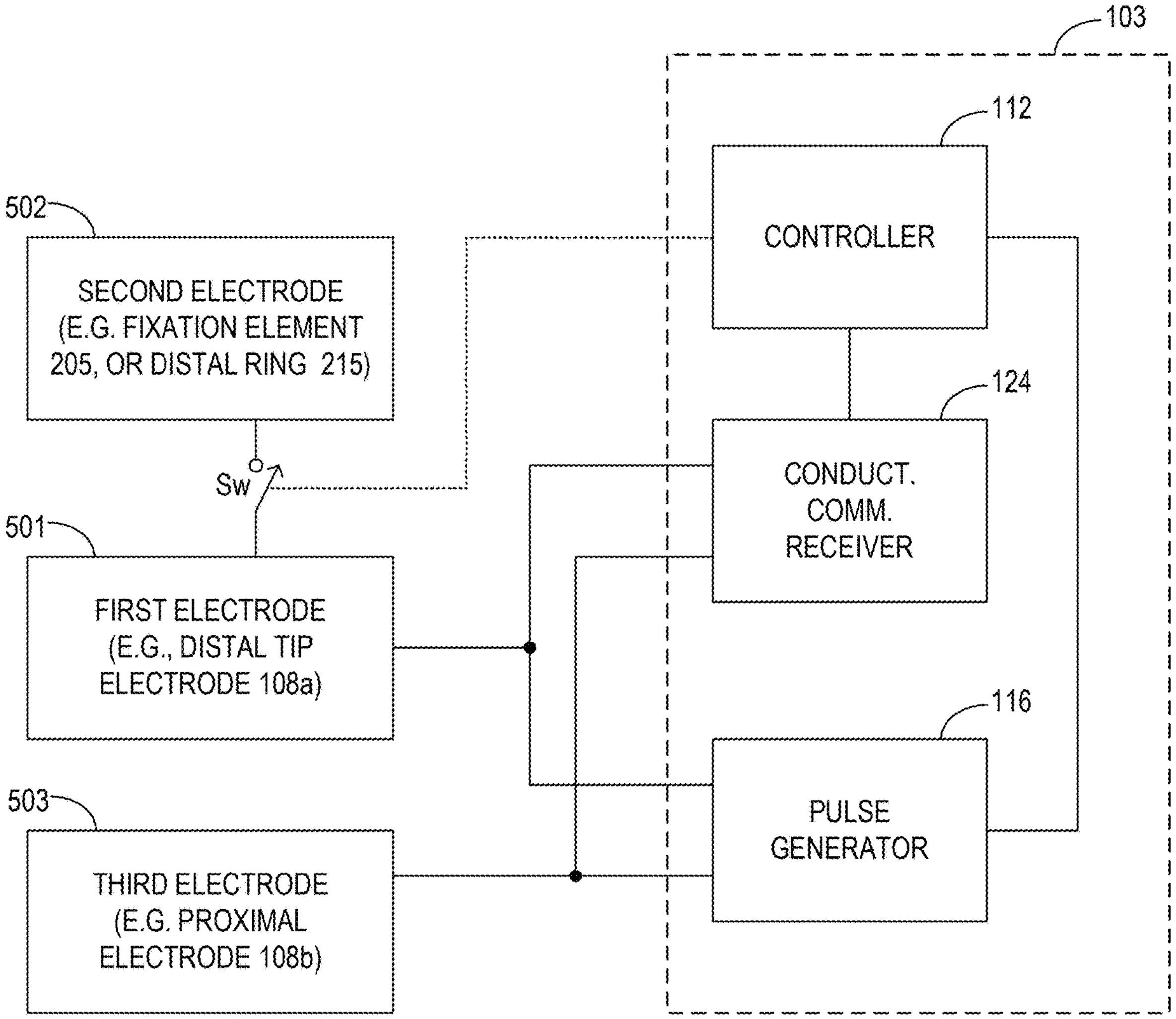
FIGS. 5A-5F are high level block diagrams used to describe various different embodiments of the present technology where different sets of electrodes are used for delivering stimulation pulses than are used for transmitting and/or receiving conductive communication pulses in order to provide for increased device longevity while also providing for conductive communication of acceptable quality.

FIG. 5A is a high level block diagram that shows just some of the elements of the LP 102 (or other type of implantable leadless biostimulator) introduced above with reference to FIGS. 1B and 2A. Referring to FIG. 5A, shown therein is the controller 112, the pulse generator 116, and the conductive communication receiver 124, additional details of which were described above with reference to FIG. 1B. Also shown in FIG. 5A are a first electrode 501, a second electrode 502, and a third electrode 503. For much of the following discussion it is assumed that the first electrode 501 is the distal tip electrode 108*a*, the second electrode 502 is the fixation element 205, and the third electrode is the proximal electrode 108*b*, all of which are shown in and described above with reference to FIG. 2A, as well as other FIGS. In certain alternative embodiments, the electrically conductive distal ring 215 (shown in FIG. 2C) is the second electrode 502. In the embodiment described with reference to FIG. 5A, as well as the embodiments described below with reference to FIGS. 5B and 5C, the first electrode 501 (e.g., the distal tip electrode 108*a*) and the second electrode 502 (e.g., the fixation element 205, or the electrically conductive distal ring 215) are each configured such that a respective electrically conductive surface area thereof is configured to be in physical contact with patient tissue of a patient within which the implantable leadless biostimulator is implanted, and such that the electrically conductive surface area of the second electrode 502 (e.g., the fixation element 205, or the electrically conductive distal ring 215) that is configured to be in physical contact with the patient tissue is greater than the electrically conductive surface area of the first electrode 501 (e.g., the distal tip electrode 108*a*) that is configured to be in physical contact with the patient tissue. FIG. 5A also shows a switch Sw that is controlled, by the controller 112, to selectively electrically connect the second electrode 502 (e.g., the fixation element 205, or the electrically conductive distal ring 215) to the first electrode 501 (e.g., the distal tip electrode 108*a*), and selectively electronically disconnect the second electrode 502 from the first electrode 501. The switch Sw can be implemented, e.g., using a bipolar junction transistor (BJT), a Metal Oxide Semiconductor Field Effect Transistor (MOSFET), an Insulated Gate Bipolar Transistor (IGBT), or a Silicon Controlled Rectifier (SCR), but is not limited thereto.

Still referring to FIG. 5A, the pulse generator 116 is shown as being electrically connected to the first electrode 501 (e.g., the distal tip electrode 108*a*) and the third electrode (e.g., the proximal electrode 108*b*). Similarly, the conductive communication receiver 124 is shown as being electrically connected to the first electrode 501 (e.g., the distal tip electrode 108*a*) and the third electrode (e.g., the proximal electrode 108*b*). Accordingly, in this embodiment, a differential signal provided to the conductive communication receiver 124 is sensed between the first electrode 501 (e.g., the distal tip electrode 108*a*) and the third electrode (e.g., the proximal electrode 108*b*). In the embodiment of FIG. 5A (as well as the embodiment of FIG. 5B), the pulse generator 116 is used to produce both stimulation pulses, as well as conductive communication pulses. In certain such embodiments, the stimulation pulses produced by the pulse generator 116 are above a capture threshold, and the conductive communication pulses produced by the pulse generator are below the capture threshold.

Still referring to FIG. 5A, in accordance with certain embodiments of the present technology, the controller 112 controls the switch Sw such that the second electrode 502 (e.g., the fixation element 205, or the electrically conductive distal ring 215) is electrically disconnected from the first electrode 501 (e.g., the distal tip electrode 108*a*) when the pulse generator 116 is caused (by the controller 112) to produce one or more stimulation pulses, such that the stimulation pulse(s) is/are delivered using the first electrode 501 (e.g., the distal tip electrode 108*a*) and the third electrode 503 (e.g., the proximal electrode 108*b*). During the delivery of such stimulation pulse(s), the first electrode 501 (e.g., the distal tip electrode 108*a*) may function as the stimulation electrode, and the third electrode (e.g., the proximal electrode 108*b*) may function as the return electrode. In accordance with certain embodiments, a first portion of the first electrode 501 (e.g., the distal tip electrode 108*a*) is covered by an insulator coating and a further portion of the first electrode 501 (e.g., the distal tip electrode 108*a*) is devoid of the insulator coating in order to achieve a higher effective impedance (aka, tissue resistance) than would be achieved if an entirety of the first electrode 501 (e.g., the distal tip electrode 108*a*) was devoid of the insulator coating. This partial coating of the first electrode 501 (e.g., the distal tip electrode 108*a*) with an insulator beneficially increases the longevity of the implantable leadless biostimulator compared to if an entirety of the first electrode 501 (e.g., the distal tip electrode 108*a*) was devoid of the insulator coating. For example, assuming the effective impedance (aka tissue resistance) of the first electrode 501 (e.g., the distal tip electrode 108*a*) entirely devoid of the insulator coating is 300 Ohms, and assuming pacing is performed at a rate of 60 beats per minute (bpm), using 2.5 Volt (V) stimulation pulses having a pulse width of 0.4 milliseconds (msec), by applying an insulator coating to a portion of the first electrode 501 (e.g., the distal tip electrode 108*a*) to increase its effective impedance (aka tissue resistance) from 300 Ohms to 740 Ohms, the longevity of the implantable leadless biostimulator can be increased by over 60% from about 4.5 years to about 7.5 years.

In such embodiments, the controller 112 also controls the switch Sw such that the second electrode 502 (e.g., the fixation element 205, or the electrically conductive distal ring 215) is electrically connected to the first electrode 501 (e.g., the distal tip electrode 108*a*) when the pulse generator 116 is caused (by the controller 112) to produce one or more conductive communication pulses, such that the conductive communication pulse(s) is/are delivered using the first electrode 501 (e.g., the distal tip electrode 108*a*) and the second electrode 502 (e.g., the fixation element 205, or the electrically conductive distal ring 215) electrically connected to one another, and using the third electrode 503 (e.g., the proximal electrode 108*b*). Additionally, the switch Sw electrically connects the second electrode 502 (e.g., the fixation element 205, or the electrically conductive distal ring 215) to the first electrode 501 (e.g., the distal tip electrode 108*a*) during at least a portion of the time (and preferably the entire time) conductive communication pulses are being received by the implantable leadless biostimulator (e.g., the LP 102) that includes the electrodes. Beneficially, by electrically connecting the second electrode 502 (e.g., the fixation element 205, or the electrically conductive distal ring 215) to the first electrode 501 (e.g., the distal tip electrode 108*a*) during the transmission and/or reception of conductive communication pulses, the significant increase in the electrically conductive surface area that is in physical contact with the patient tissue significantly increases the strength of conductive communication pulses that are transmitted and received. When the second electrode 502 (e.g., the fixation element 205, or the electrically conductive distal ring 215) and the first electrode 501 (e.g., the distal tip electrode 108*a*) are electrically connected to one another by the switch Sw during reception of conductive communication pulses, a differential signal provided to the conductive communication receiver 124 is sensed between the third electrode 503 and the connected together first and second electrodes 501, 502 (which act as a single electrode having an electrically conductive surface area that is greater than either of the electrodes 501, 502 alone). More generally, wherever two electrically isolated electrodes are connected to the same receiver, it can be said that a different signal that is sensed between the two electrically isolated electrodes is provided to the receiver. In such embodiments, it is possible that one of the "two" electrically isolated electrodes is provided by multiple electrodes connected together by a switch, e.g., the switch Sw.

In the embodiments described above with reference to FIG. 5A, the controller 112 controls the switch Sw to electrically disconnect the second electrode 502 (e.g., the fixation element 205, or the electrically conductive distal ring 215) from the first electrode 501 (e.g., the distal tip electrode 108*a*), or vice versa, during periods of time during which stimulation pulses produced by the pulse generator 116 are to be delivered to patient tissue (e.g., cardiac tissue) using the first electrode 501 (e.g., the distal tip electrode 108*a*) and the third electrode 503 (e.g., the proximal electrode 108*b*). Additionally, the controller 112 controls the switch Sw to electrically connect the second electrode 502 (e.g., the fixation element 205, or the electrically conductive distal ring 215) and the first electrode 501 (e.g., the distal tip electrode 108*a*) during other periods of time during which conductive communication pulses produced by the pulse generator 116 are to be transmitted through patient tissue using the first electrode 501 (e.g., the distal tip electrode 108*a*) electrically connected to the second electrode 502 (e.g., the fixation element 205, or the electrically conductive distal ring 215) and using the third electrode 503 (e.g., the proximal electrode 108*b*), and/or during which conductive communication pulses are received using the first electrode 501 (e.g., the distal tip electrode 108*a*) electrically connected to the second electrode 502 (e.g., the fixation element 205, or the electrically conductive distal ring 215) and using the third electrode 503 (e.g., the proximal electrode 108*b*). In FIG. 5A, the third electrode 503 (e.g., the proximal electrode 108*b*) is shown as remaining electrically connected to one of the terminals (e.g., the return terminal) of the pulse generator 116 and to one of the terminals of the conductive communication receiver 124.

While not specifically shown in the FIG. 5A (or in any of the other FIGS., such as FIGS. 5B-5F), there can be additional switches (not shown) that are used to implement blanking of the conductive communication receiver 124 during delivery of the stimulation pulses produced by the pulse generator 116. These switches, which can be referred to as blanking switches, can be used to prevent saturation and damage to the conductive communication receiver 124 from being caused by stimulation pulses produced by the pulse generator 116 (or another pulse generator, e.g., 116*a* or 116*b*). Such blanking switches can also be controlled by the controller 112, and can be part of an analog front end, but are not limited thereto. The use of such blanking switches is already known to those of skill in the art, and thus need not be described in additional detail.

In FIG. 5A, and FIGS. 5B-5F, the elements within the dashed block labeled 103, or subsets thereof, can be referred to as circuitry 103 of an implantable leadless biostimulator, such as LP 102. Accordingly, it should be appreciated that the circuitry 103 can include, e.g., one or more of a controller 112, a conductive communication receiver 124, and a pulse generator 116. The circuitry 103 can also include one or more switches, e.g., the switches Sw shown in some of these FIGS. The circuitry 103 can also include multiple pulse generators (e.g., 116*a*, 116*b*) as shown in and discussed below with reference to FIGS. 5C-5F. While in some of FIGS. 5A-5F the switches Sw shown therein may not be within the dashed block labeled 103, it should be appreciated that such switches Sw are indeed part of the circuitry 103. The circuitry 103 can also include all, or some, of the elements described as being within the housing 110 with reference to FIG. 1B discussed above.

Figure 5B:
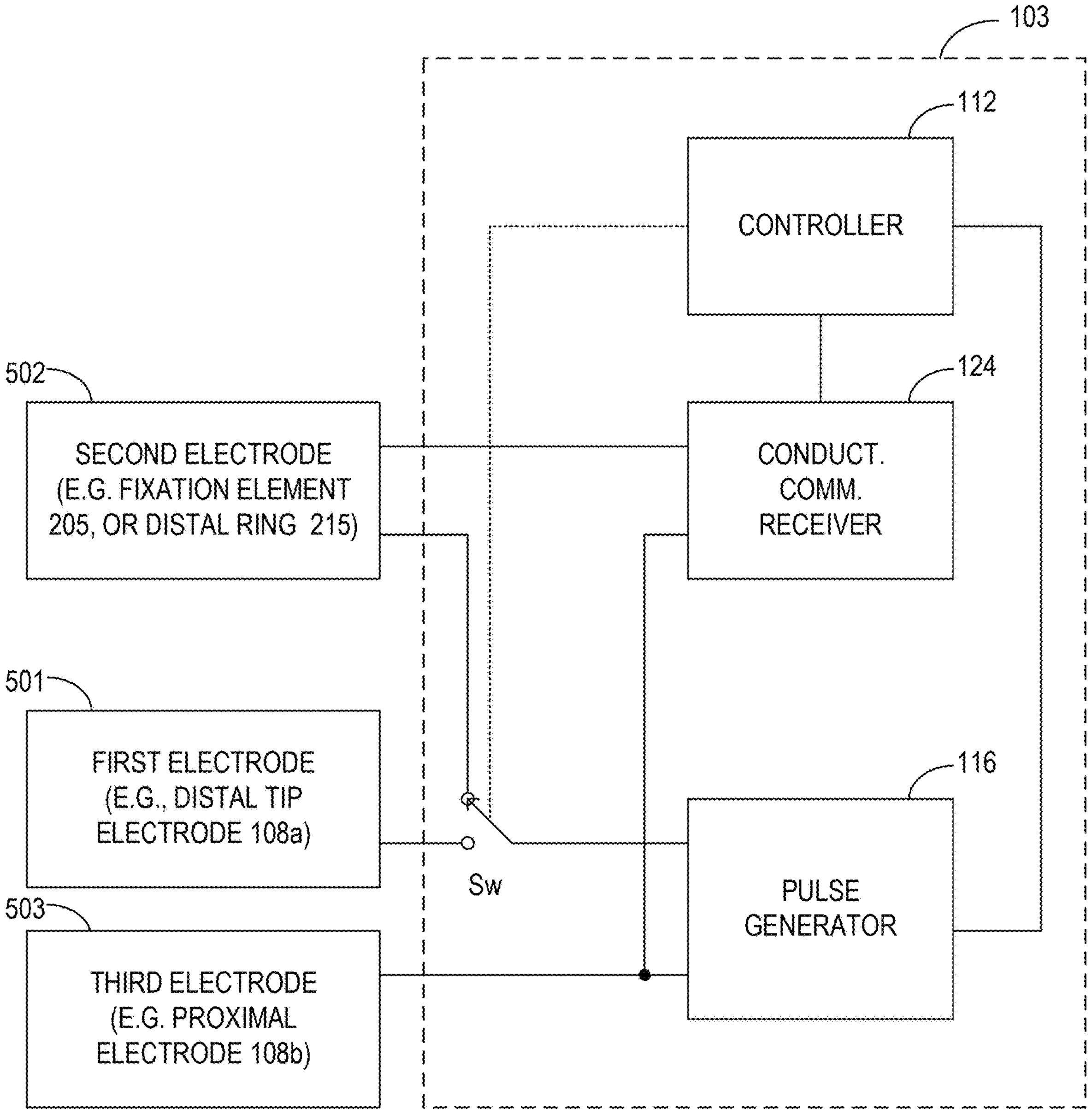

In certain alternative embodiments, which will now be described with reference to FIG. 5B, rather than using the switch Sw to selectively connect and disconnect the second electrode 502 (e.g., the fixation element 205, or the electrically conductive distal ring 215) to and from the first electrode 501 (e.g., the distal tip electrode 108*a*), the switch Sw is instead use to select between the first electrode 501 (e.g., the distal tip electrode 108*a*) and the second electrode 502 (e.g., the fixation element 205, or the electrically conductive distal ring 215). In the embodiments of FIG. 5B (as was also the case in the embodiment of FIG. 5A), the pulse generator 116 is used to produce both stimulation pulses and conductive communication pulses. In the embodiments of FIG. 5B, the controller 112 controls the switch Sw to electrically connect the first electrode 501 (e.g., the distal tip electrode 108*a*), but not the second electrode 502 (e.g., the fixation element), to the pulse generator 116 during periods of time during which stimulation pulses produced by the pulse generator 116 are to be delivered to patient tissue (e.g., cardiac tissue) using the first electrode 501 (e.g., the distal tip electrode 108*a*) and the third electrode 503 (e.g., the proximal electrode 108*b*). Additionally, the controller 112 controls the switch Sw to electrically connect the second electrode 502 (e.g., the fixation element 205, or the electrically conductive distal ring 215), but not the first electrode 501 (e.g., the distal tip electrode 108*a*), to the pulse generator 116 during other periods of time during which conductive communication pulses produced by the pulse generator 116 are to be transmitted through patient tissue using the second electrode 502 (e.g., the fixation element 205, or the electrically conductive distal ring 215) and the third electrode 503 (e.g., the proximal electrode 108*b*), and/or during which conductive communication pulses are received using the second electrode 502 (e.g., the fixation element 205, or the electrically conductive distal ring 215) and the third electrode 503 (e.g., the proximal electrode 108*b*). Beneficially, by using the second electrode 502 (e.g., the fixation element 205, or the electrically conductive distal ring 215) and the third electrode 503 (e.g., the proximal electrode 108*b*) for transmission and/or reception of conductive communication pulses, rather than the first electrode 501 (e.g., the distal tip electrode 108*a*) and the third electrode 503 (e.g., the proximal electrode 108*b*), there is a significant increase in the electrically conductive surface area that is in physical contact with the patient tissue that significantly increases the strength of conductive communication pulses that are transmitted and received. As was also the case in the embodiments described above with reference to FIG. 5A, in the embodiments of FIG. 5B it would be beneficial for a first portion of the first electrode 501 (e.g., the distal tip electrode 108*a*) to be covered by an insulator coating and a further portion of the first electrode 501 (e.g., the distal tip electrode 108*a*) to be devoid of the insulator coating in order to achieve a higher effective impedance (aka tissue resistance) than would be achieved if an entirety of the first electrode 501 (e.g., the distal tip electrode 108*a*) was devoid of the insulator coating, in order to increase the longevity of the implantable leadless biostimulator by over 60% from about 4.5 years to about 7.5 years.

In the embodiments described above with reference to FIGS. 5A and 5B, the same pulse generator 116 is used to produce both stimulation pulses and conductive communication pulses. In certain alternative embodiments, described below with reference to FIGS. 50, 5E and 5F, there are two separate pulse generators 116*a* and 116*b*, with the pulse generator 116*a* being used to produce stimulation pulses, and the pulse generator 116*b* being used to produce conductive communication pulses. In such embodiments, the stimulation pulses produced by the pulse generator 116*a* are above a capture threshold, and the conductive communication pulses produced by the pulse generator 116*b* are below the capture threshold.

Figure 5C:
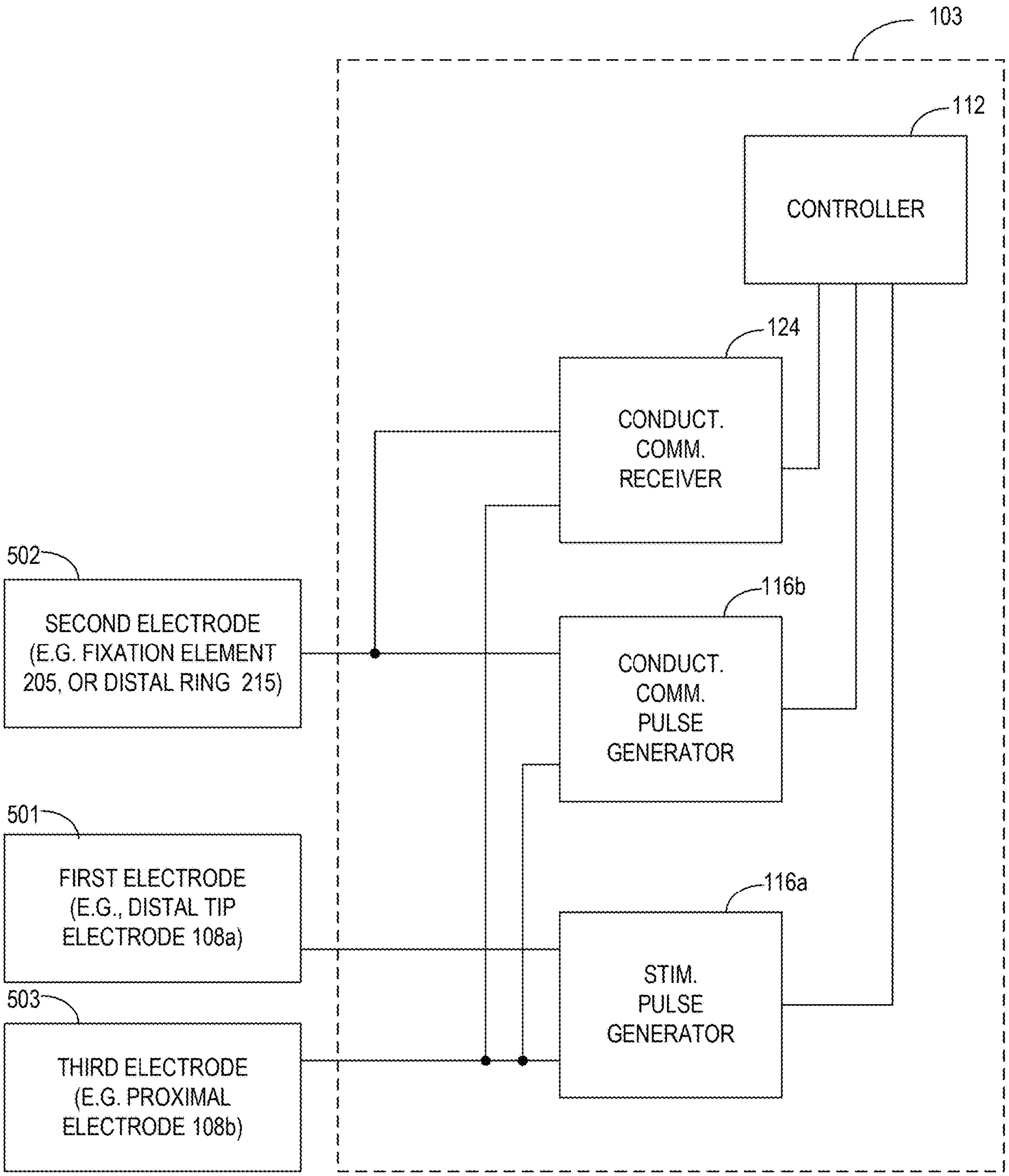

Referring to FIG. 5C, the terminals of the pulse generator 116*a* are shown as being connected to the first electrode 501 (e.g., the distal tip electrode 108*a*) and the third electrode 503 (e.g., the proximal electrode 108*b*). The terminals of the other pulse generator 116*b* are shown as being connected to the second electrode 502 (e.g., the fixation element 205, or the electrically conductive distal ring 215) and the third electrode 503 (e.g., the proximal electrode 108*b*). The terminals of the conductive communication receiver 124 are shown as being connected to the second electrode 502 (e.g., the fixation element 205, or the electrically conductive distal ring 215) and the third electrode 503 (e.g., the proximal electrode 108*b*). By using the first electrode 501 (e.g., the distal tip electrode 108*a*) that has a relatively small electrically conductive surface area in contact with patient tissue (e.g., because it is partially coated with an insulator), along with the third electrode (e.g., the proximal electrode 108*b*), to deliver stimulation pulses (e.g., pacing pulses), a higher effective impedance (aka tissue resistance) is achieved to increase battery longevity, and thus, device longevity. By using the second electrode 502 (e.g., the fixation element 205, or the electrically conductive distal ring 215) that has a relatively large electrically conductive surface area in contact with patient tissue along with the third electrode 503 (e.g., the proximal electrode 108*b*), to deliver and receive conductive communication pulses, a lower effective impedance (aka tissue resistance) is achieved to improve conductive communication quality. In the embodiments of FIG. 5C, the controller 112 controls the pulse generator 116*a* to produce stimulation pulses during periods of time to cause the stimulation pulses produced by the pulse generator 116*a* to be delivered using the first electrode 501 (e.g., the distal tip electrode 108*a*) and the third electrode 503 (e.g., the proximal electrode 108*b*). Additionally, the controller 112 controls the pulse generator 116*b* to produce conductive communication pulses during other periods of time to cause the conductive communication pulses produced by the pulse generator 116*b* to be transmitted through patient tissue using the second electrode 502 (e.g., the fixation element 205, or the electrically conductive distal ring 215) and the third electrode 503 (e.g., the proximal electrode 108*b*). In the embodiments described with reference to FIG. 5C there is no switch to select between the first electrode 501 (e.g., the distal tip electrode 108*a*) and the second electrode 502 (e.g., the fixation element 205, or the electrically conductive distal ring 215). Also, in the embodiments described with reference to FIG. 5C there is no switch to selectively electrically connect or disconnect the second electrode 502 (e.g., the fixation element 205, or the electrically conductive distal ring 215) from the first electrode 501 (e.g., the distal tip electrode 108*a*).

Figure 5D:
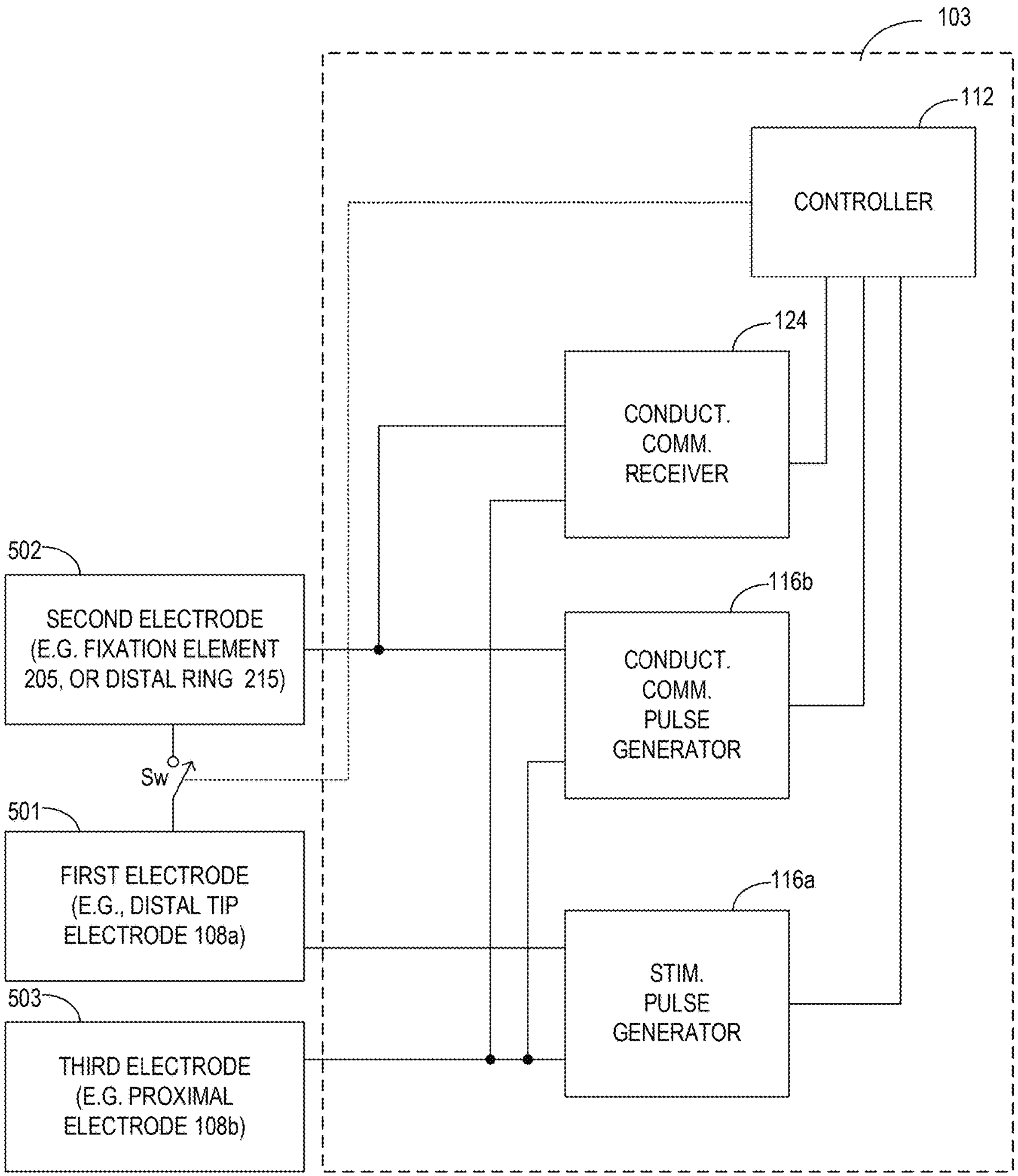

Referring now to FIG. 5D, which is a slight variation to the embodiments of FIG. 50, a switch Sw is used to selectively electrically connect or disconnect the second electrode 502 (e.g., the fixation element 205, or the electrically conductive distal ring 215) to and from the first electrode 501 (e.g., the distal tip electrode 108*a*). More specifically, the controller 112 controls the switch Sw to electrically connect the second electrode 502 (e.g., the fixation element 205, or the electrically conductive distal ring 215) to the first electrode 501 (e.g., the distal tip electrode 108*a*) when the conductive communication receiver 124 is receiving conductive communication pulses from another IMD (e.g., another LP 102, the ICM 104, or the ICD 106) or the external device 109, as well as when the pulse generator 116*b* produces conductive communication pulses that are to be transmitted to the other IMD (e.g., another LP 102, the ICM 104, or the ICD 106) or the external device 109. Further, the controller 112 controls the switch Sw to electrically disconnect the second electrode 502 (e.g., the fixation element 205, or the electrically conductive distal ring 215) from the first electrode 501 (e.g., the distal tip electrode 108*a*) when the pulse generator 116*a* produces stimulation pulses that are to be delivered to patient tissue.

Figure 5E:
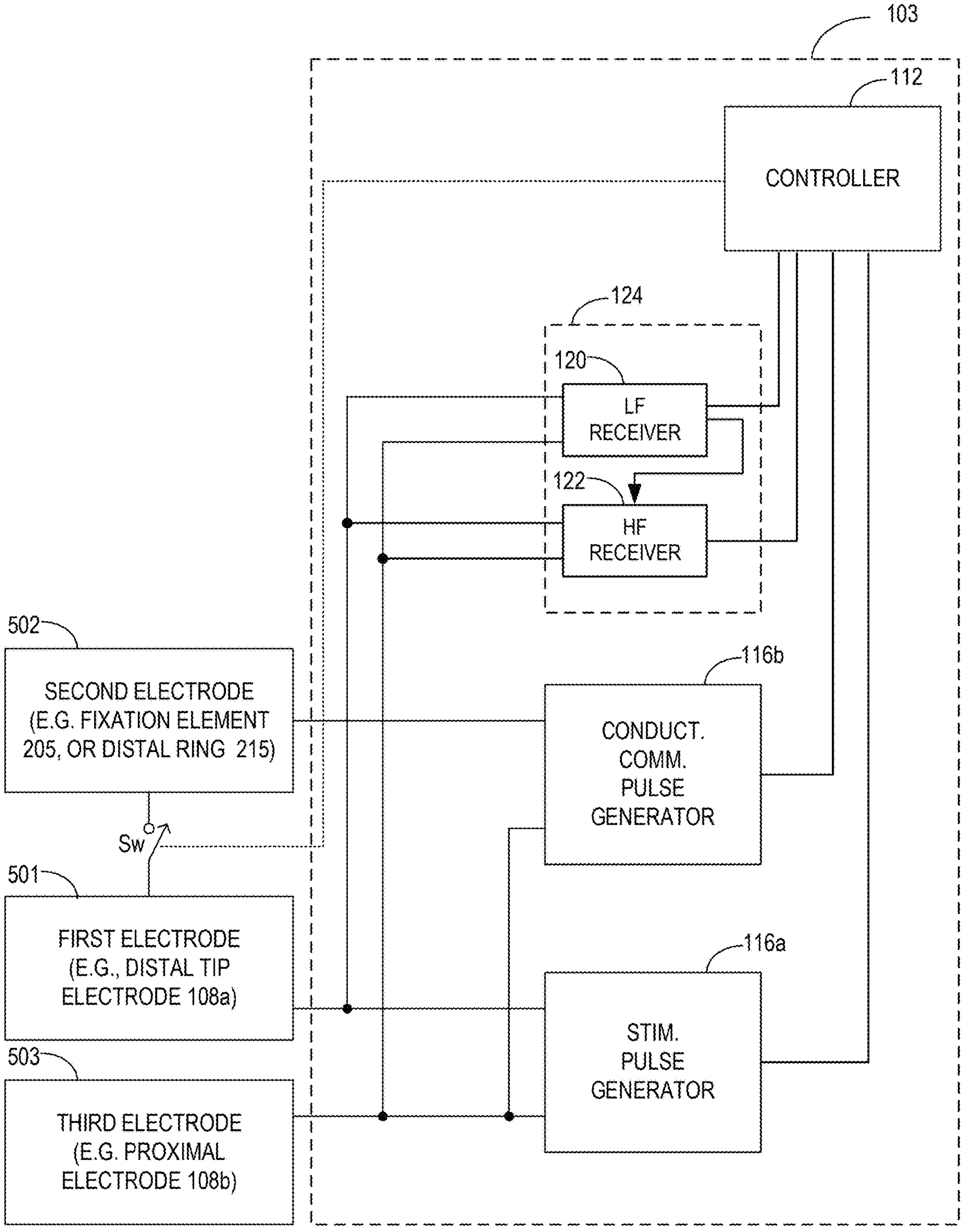

Referring now to FIG. 5E, in the embodiment shown therein, the first electrode 501 (e.g., the distal tip electrode 108*a*) and the third electrode 503 (e.g., the proximal electrode 108*b*) are connected to the stimulation pulse generator 116*a*, and the second electrode 502 (e.g., the fixation element 205 or the distal ring 215) and the third electrode 503 (e.g., the proximal electrode 108*b*) are connected to the conductive communication pulse generator 116*b*. The first electrode 501 (e.g., the distal tip electrode 108*a*) and the third electrode 503 (e.g., the proximal electrode 108*b*) are connected to the LF receiver 120 (of the conductive communication receiver 124), and the controller 112 controls the switch Sw to cause the second electrode 502 (e.g., the fixation element 205 or the distal ring 215) to be electrically disconnected from the first electrode 501 when the LF receiver 120 is monitoring for a LF wakeup pulse from another device. In response to the LF receiver 120 receiving the LF wakeup pulse from the other device, the LF receiver 120 wakes up the HF receiver 122, and the controller 112 controls the switch Sw to electrically connect the second electrode 502 (e.g., the fixation element 205 or the distal ring 215) to the first electrode 501 (e.g., the distal tip electrode 108*a*), so that the HF receiver 122 receives HF conductive communication pulses using the first and the second electrodes 501, 502 (e.g., the distal tip electrode 108*a* and the fixation element 205 or the distal ring 215) electrically connected to one another, and using the third electrode 503 (e.g., the proximal electrode 108*b*). In other words, the HF receiver 122 receives a signal sensed between the electrically connected to one another first and the second electrodes 501, 502 (acting as one larger electrode) and the third electrode 503. In another embodiment, the two pulse generators 116*a* and 116*b* in FIG. 5E are replaced with a single pulse generator 116 that produces both the stimulation pulses and the conductive communication pulses.

Figure 5F:
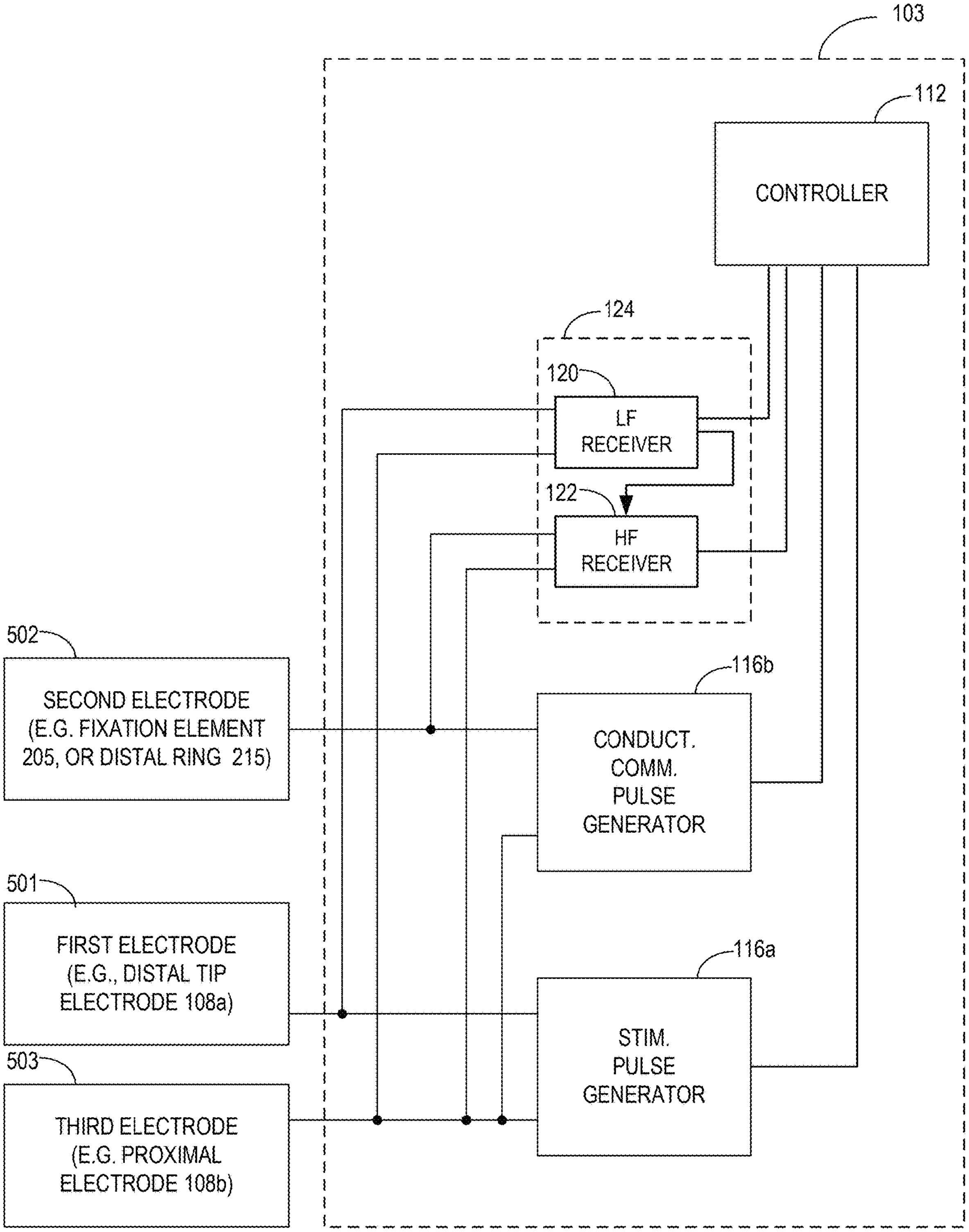

Referring now to FIG. 5F, in the embodiment shown therein: the first electrode 501 (e.g., the distal tip electrode 108*a*) and the third electrode 503 (e.g., the proximal electrode 108*b*) are connected to the stimulation pulse generator 116*a*; the first electrode 501 (e.g., the distal tip electrode 108*a*) and the third electrode 503 (e.g., the proximal electrode 108*b*) are connected to the LF receiver 120 (of the conductive communication receiver 124); the second electrode 502 (e.g., the fixation element 205 or the distal ring 215) and the third electrode 503 (e.g., the proximal electrode 108*b*) are connected to the conductive communication pulse generator 116*b*; and the second electrode 502 (e.g., the fixation element 205 or the distal ring 215) and the third electrode 503 (e.g., the proximal electrode 108*b*) are connected to the HF receiver 122 (of the conductive communication receiver 124). The embodiment of FIG. 5F provides for a simplified design without any need for one or more switches (e.g., Sw) that is/are specifically used to selectively connect/disconnect electrodes to/from different ones of the pulse generators 116*a*, 116*b*, and/or receivers 120, 122. (However, as in the other embodiments and as mentioned above, the embodiment of FIG. 5F can include blanking switches, which are not shown.) Additionally, having separate LF and HF receivers 120, 122 allows each of the receivers 120, 122 to be optimized for expected target signals (having an expected target amplitude range, an expected target frequency/sampling rate range, etc.), which can prevent or at least reduce saturation of the HF receiver 122 due to LF signal coupling from the larger second electrode 502 (e.g., the fixation element 205, or distal ring 215). In another embodiment, the two pulse generators 116*a* and 116*b* in FIG. 5F are replaced with a single pulse generator 116 that produces both the stimulation pulses and the conductive communication pulses.

In each of the above described embodiments, the first electrode 501 (e.g., the distal tip electrode 108*a*) can be partially coated with an insulator to optimize the surface area of the first electrode 501 that is in contact with patient tissue that it to be selectively stimulated (e.g., paced) to achieve an effective impedance (aka tissue resistance) used for stimulating (e.g., pacing) that is within a desired range. Similarly, the second electrode 502 (e.g., the fixation element 205, or the electrically conductive distal ring 215) can be partially coated with an insulator to optimize the surface area of the second electrode 502 that is in contact with patient tissue to achieve an effective impedance (aka tissue resistance) used for conductive communication that is within another desired range. Additionally, the third electrode 503 (e.g., the proximal electrode 108*b*) can be partially coated with an insulator to optimize the surface area of the third electrode 503 to achieve an effective impedance (aka tissue resistance) within a further desired range. The insulator coating can also be referred to herein as an insulator layer, an insulative layer, an insulative coating, or the like. The portion of an electrode that is coated by an insulator can be referred to as the insulated portion or the insulative portion, and the portion of an electrode that is not covered by the insulator can be referred to as an electrically conductive portion, or more succinctly as a conductive portion, a non-electrically insulated portion, a portion devoid of an insulator, or the like. The electrically conductive portion of an electrode can be contiguous, or alternatively, can be discontiguous pattern (e.g., have polka dot like pattern, but not limited thereto). The insulator that is used to coat a portion of the electrodes can be, e.g., perylene or a similar biocompatible insulating compound that is able to sufficiently electrically insulate coated portions of an electrode from patient tissue.

In each of the above described embodiments, the third electrode 503 (e.g., the proximal electrode 108*b*) was described as being part of the set of electrodes used for delivering stimulation, as well as being part of the set of electrodes used for transmitting and/or receiving conductive communication pulses. In such embodiments, the set of electrodes used for delivering stimulation and the set of electrodes used for conductive communication share a common electrode, i.e., the third electrode 503 (e.g., the proximal electrode 108*b*). If the implantable leadless biostimulator includes more than three electrodes, it would be possible for the set of electrodes used for delivering stimulation and the set of electrodes used for conductive communication to not share any electrodes. This would be possible, for example, if a leadless pacemaker (or other type of implantable biostimulator) included more than one proximal electrode, e.g., if the retrieval feature 242 on the proximal end of the leadless pacemaker (or other type of implantable leadless biostimulator) was made of an electrically conductive material and could be used as a fourth electrode. Other variations are also possible and with the scope of the embodiments described herein. While the implantable leadless biostimulators described herein are often described as being leadless pacemakers, the implantable leadless biostimulators can by other types of biostimulators, such as, but not limited to, implantable leadless neurostimulators.

Figure 6:
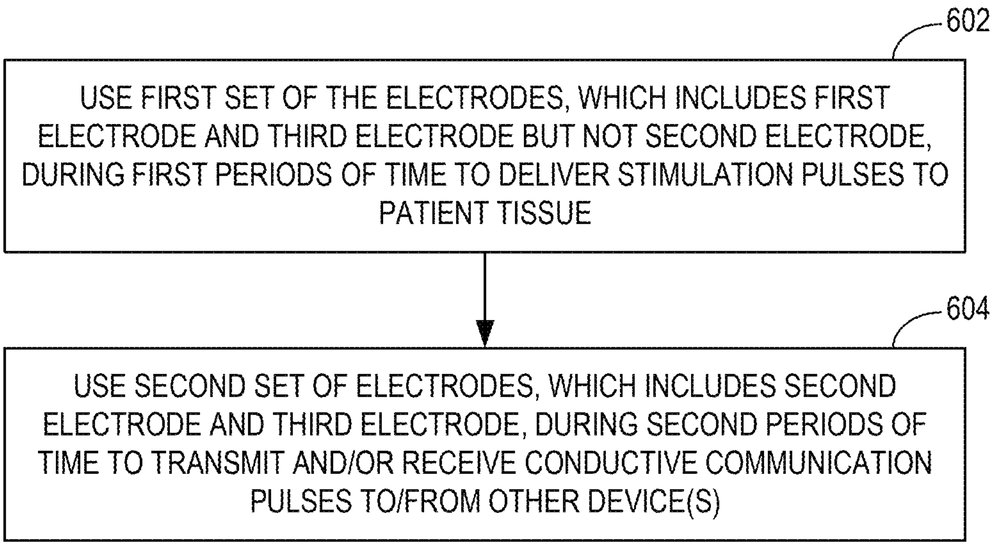
FIG. 6 is a high level flow diagram used to summarize methods of embodiments of the present technology that are for use by an implantable leadless biostimulator to provide for increased device longevity while also providing for conductive communication of acceptable quality.

The high level flow diagram of FIG. 6 will now be used to summarize methods according to certain embodiments of the present technology that are for use by an implantable leadless biostimulator comprising three or more electrodes including a first electrode 501, a second electrode 502, and one or more additional electrodes (e.g., the third electrode 503), wherein the first electrode 501 and the second electrode 502 are each configured such that a respective electrically conductive surface area thereof is in physical contact with patient tissue of a patient within which the implantable leadless biostimulator is implanted, and such that the electrically conductive surface area of the second electrode 502 that is in physical contact with the patient tissue is greater than the electrically conductive surface area of the first electrode 501 that is in physical contact with the patient tissue. Referring to FIG. 6, step 602 involves using a first set of the electrodes, which includes the first electrode 501 but not the second electrode 502, during first periods of time to deliver stimulation pulses to the patient tissue. Still referring to FIG. 6, step 604 involves using a second set of the electrodes, which includes the second electrode 502, during second periods of time to at least one of transmit conductive communication pulses to, or receive conductive communication pulses from, one or more other devices 104, 106, 109 (and/or another implantable leadless biostimulator 102). Each of the first and the second set of electrodes, used at steps 602 and 604, includes a respective different plurality of the three or more electrodes. For example, as was the case in FIG. 5A, the first set of electrodes used at step 602 can include the first electrode 501 (electrically disconnected from the second electrode 502 by the switch Sw) and the third electrode 503; and the second set of electrodes used at step 604 can include the first electrode 501 electrically connected to the second electrode 502 by the switch Sw, and the third electrode 503. For another example, as was the case in FIGS. 5B and 50, the first set of electrodes used at step 602 can include the first electrode 501 and the third electrode 503; and the second set of electrodes used at step 604 can include the second electrode 502 and the third electrode 503. Other variations are also possible and within the scope of the embodiments described herein. It is noted that it would also be possible that the set of electrodes used for transmitting conductive communication pulses to one or more other devices 104, 106, 109 (and/or another implantable leadless biostimulator 102) can differ from the set of electrodes used to receive conductive communication pulses from the other device(s), e.g., as was described above with reference to FIG. 5D.

In certain embodiments, the first electrode 501 referred to in FIGS. 5A-5F and 6 is a distal tip electrode (e.g., 108*a*) located at a distal end of an LP 102, or other type of implantable leadless biostimulator. In certain such embodiments, the second electrode 502 is a fixation element (e.g., 205) configured to physically attach the implantable leadless biostimulator to the patient tissue. Alternatively, the second electrode 502 is an electrically conductive distal ring (e.g., 215). Other variations are also possible, and within the scope of the embodiments described herein. The one or more additional electrodes can be, e.g., a proximal electrode (e.g., 108*b*) located on a proximal portion of the implantable leadless biostimulator, but is not limited thereto.

In certain embodiments, the implantable leadless biostimulator comprises a leadless pacemaker 102, the distal tip electrode 108*a* is located at a distal end of the leadless pacemaker 102, the fixation element 205 extends from a distal portion of the leadless pacemaker 102, and the proximal electrode 108*b* is located on a proximal portion of the leadless pacemaker 102. In such embodiments, the patient tissue, that the fixation element 205 is configured to physically attach the leadless pacemaker to is cardiac tissue. Further, in such embodiments, the electrically conductive surface area of the fixation element 205 that is in physical contact with the cardiac tissue is greater than the electrically conductive surface area of the distal tip electrode 108*a* that is in physical contact with the cardiac tissue. Examples of the distal tip electrode 108*a* were described above with reference to FIGS. 2B and 2C.

In certain embodiments, the first set of the electrodes (used during first periods of time to deliver stimulation pulses to the patient tissue at step 602) includes the distal tip electrode 108*a* and the proximal electrode 108*b*, and the second set of electrodes (used during second periods of time to at least one of transmit conductive communication pulses to, or receive conductive communication pulses from, the one or more other devices at step 604) includes the fixation element 205 and the proximal electrode 108*b*.

In certain embodiments, the first set of the electrodes (used during first periods of time to deliver stimulation pulses to the patient tissue at step 602) includes the distal tip electrode 108*a* and the proximal electrode 108*b*, and the second set of electrodes (used during second periods of time to at least one of transmit conductive communication pulses to, or receive conductive communication pulses from, the one or more other devices at step 604) includes the distal tip electrode 108*a* and the fixation element 205 electrically connected to one another (e.g., by the switch Sw) and also includes the proximal electrode 108*b*.

In certain such embodiments, such as those described above with reference to FIG. 5A (where the same pulse generator 116 produces both stimulation pulses and conductive communication pulses), step 602 includes controlling a switch Sw to cause the fixation element 205 to be electrically disconnected from the distal tip electrode 108*a* during the first periods of time during which stimulation pulses are to be delivered to the patient tissue using the distal tip electrode 108*a* and the proximal electrode 108*b*, and step 604 includes controlling the switch Sw to cause the fixation element 205 to be electrically connected to the distal tip electrode 108*a* during the second periods of time during which conductive communication pulses are transmitted to and/or received from the one or more other devices 104, 106, 109 (and/or another implantable leadless biostimulator 102).

In alternative embodiments, such as those described above with reference to FIG. 5B (again, where the same pulse generator 116 produces both stimulation pulses and conductive communication pulses), step 602 includes controlling a switch Sw to cause the distal tip electrode 108*a* and the proximal electrode 108*b* to be electrically connected to terminals of the pulse generator 116 during the first periods of time during which stimulation pulses are delivered to the patient tissue using the distal tip electrode 108*a* and the proximal electrode 108*b*, and step 604 includes controlling the switch Sw to cause the fixation element 205 and the proximal electrode 108*b* to be electrically connected to the terminals of the pulse generator during the second periods of time during which the conductive communication pulses produced by the pulse generator are transmitted to the one or more other devices using the fixation element 205 and the proximal electrode 108*b*.

In still other embodiments, such as those described above with reference to FIGS. 5C, 5D and 5F (where a different pulse generator is used to produce conductive communication pulses than the pulse generator that produces stimulation pulses), step 602 includes using a first pulse generator 116*a* to produce the stimulation pulses during the first periods of time, and step 604 includes using a second pulse generator 116*b* to produce the conductive communication pulses during the second periods of time.

In the embodiment of FIG. 5C, the stimulation pulses produced by the first pulse generator 116*a* are delivered using the distal tip electrode 108*a* (acting as the first electrode 501) and the proximal electrode 108*b* (acting as the third electrode 503) during the first periods of time at step 602, and the conductive communication pulses produced by the second pulse generator 116*b* are transmitted using the fixation element 205 (acting as the second electrode 502) and the proximal electrode 108*b* (acting as the first electrode 501) during the second periods of time at step 604. According, in such an embodiment the first set of electrodes include the first electrode 501 and the third electrode 503, and the second set of electrodes includes the second electrode 502 and the third electrode 503.

In the embodiment of FIG. 5D, the stimulation pulses produced by the first pulse generator 116*a* are delivered using the distal tip electrode 108*a* (acting as the first electrode 501) and the proximal electrode 108*b* (acting as the third electrode 503) during the first periods of time at step 602 (while the second electrode 502 is electrically disconnected from the first electrode by the switch Sw), and the conductive communication pulses produced by the second pulse generator 116*b* are transmitted using the fixation element 205 (acting as the second electrode 502) electrically connected by the switch Sw to the distal tip electrode 108*a* (acting as the first electrode 501) and using the proximal electrode 108*b* (acting as the third electrode 503) during the second periods of time at step 604. According, in such an embodiment the first set of electrodes include the first electrode 501 and the third electrode 503, and the second set of electrodes includes the first and second electrodes 501, 502 electrically connected to one another and the third electrode 503.

In the embodiment of FIG. 5F, the stimulation pulses produced by the first pulse generator 116*a* are delivered using the distal tip electrode 108*a* (acting as the first electrode 501) and the proximal electrode 108*b* (acting as the third electrode 503) during the first periods of time at step 602, and the conductive communication pulses produced by the second pulse generator 116*b* are transmitted using the fixation element 205 (acting as the second electrode 502) and using the proximal electrode 108*b* (acting as the third electrode 503) during the second periods of time at step 604. According, in such an embodiment the first set of electrodes include the first electrode 501 and the third electrode 503, and the second set of electrodes includes the second electrode 502 and the third electrode 503.

In the above described embodiments where the distal tip electrode 108*a* and the proximal electrode 108*b* are used to deliver stimulation pulses, the distal tip electrode 108*a* operates as a stimulation electrode and the proximal electrode 108*b* operates as a return electrodes.

In accordance with certain embodiments, e.g., such as the embodiments shown in FIG. 1B and FIG. 5F, the implantable leadless biostimulator includes an LF receiver 120 and a HF receiver 122. The HF receiver 122 is normally disabled to conserve power. The LF receiver 120 is configured to receive a LF wakeup conductive communication pulse and in response thereto enable the HF receiver 122 so that the HF receiver 122 can receive HF conductive communication pulses from another device. In certain such embodiments, a method can include controlling a switch Sw to cause the fixation element 205 to be electrically disconnected from the distal tip electrode 108*a* while the LF receiver 120 of the implantable leadless biostimulator monitors for the LF wakeup conductive communication pulse. The method can also include controlling the switch Sw to cause the fixation element 205 to be electrically connected to the distal tip electrode 108*a*, in response to the LF receiver 120 receiving the LF wakeup conductive communication pulse and enabling the HF receiver 122 so that the HF receiver 122 can receive HF conductive communication pulses from the other device. The method can also include controlling a switch Sw to electrically connect the fixation element 205 to the distal tip electrode 108*a* while monitoring for an external device's open link command sent in response to an advertisement sequence that was transmitted by the LP and/or while at least one frame is being conductively communicated between the implantable leadless biostimulator and the external device. Additionally, the method can include controlling the switch Sw to electrically disconnect the fixation element 205 from the distal tip electrode 108*a* while not monitoring for an external device's open link command sent in response to an advertisement sequence that was transmitted by the LP and/or while no frame is being conductively communicated between the implantable leadless biostimulator and the external device. While not specifically shown in FIGS. 5A-5D, in accordance with certain embodiments, the conductive communication receivers 124 shown in those FIGS. can include an LF receiver 120 and a HF receiver 122, as was specially shown in FIG. 1B and FIG. 5F.

In accordance with certain embodiments, the same set of electrodes (e.g., one of the above described second set of electrodes) that is used for performing conductive communication is also used for sensing an electrocardiogram (EGM) and/or other type of physiologic signal during further periods of time (when stimulation is not being delivered, and conductive communication is not being performed), which may be interspersed with the first and second periods of time discussed above with reference to FIG. 6.

Figure 7:
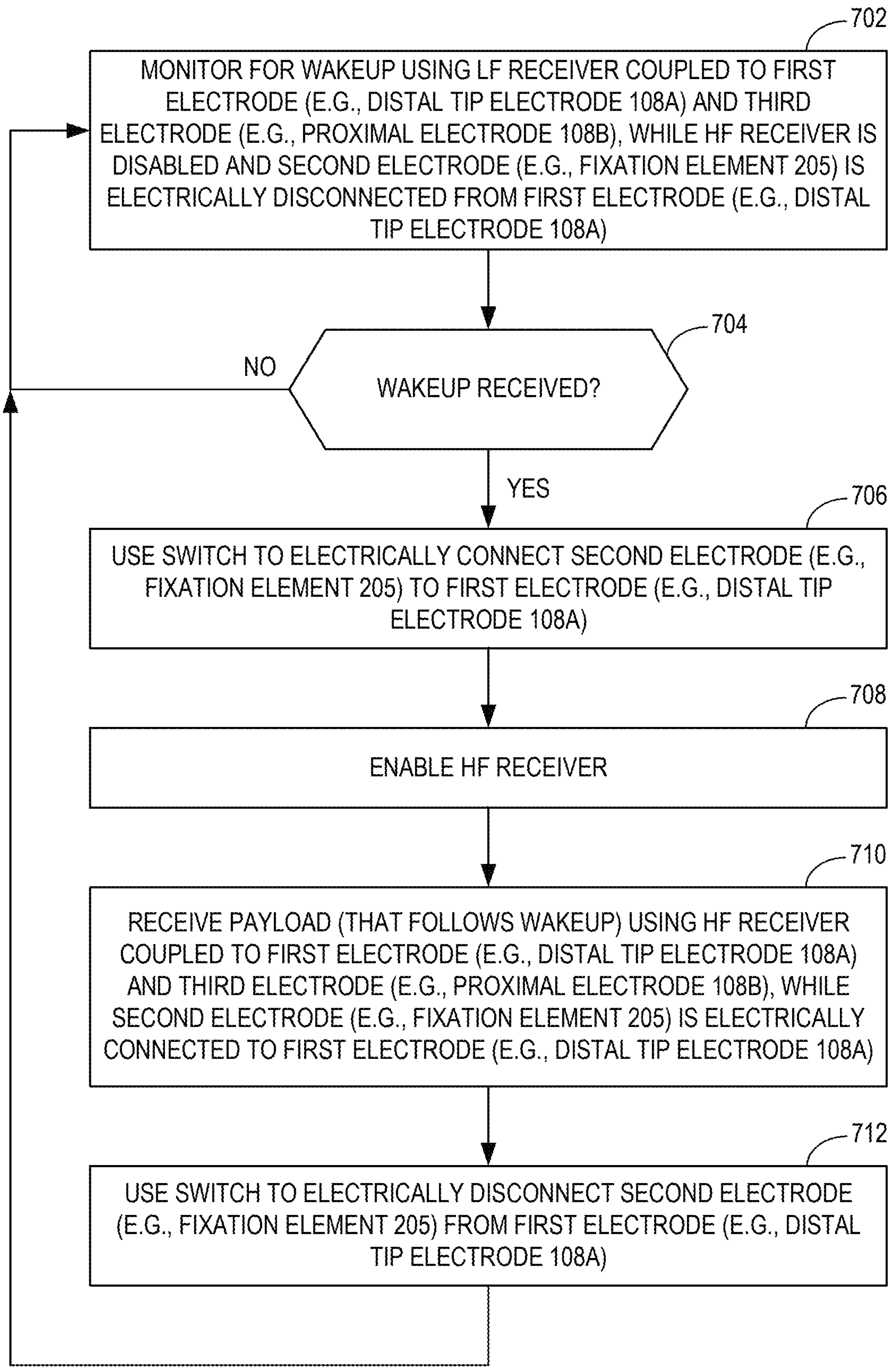
FIG. 7 is a high level flow diagram used to summarize methods according to certain embodiments of the present technology that are used by an implantable leadless biostimulator, that includes both a low frequency (LF) receiver and a high frequency (HF) receiver, to receive i2i conductive communication signals.

The high level flow diagram of FIG. 7 will now be used to summarize methods according to certain embodiments of the present technology that are used by an implantable leadless biostimulator (e.g., LP 102) that includes both a LF receiver (e.g., 120) and a HF receiver (e.g., 122), examples of which were described above with reference to FIG. 1B to receive i2i conductive communication signals. Referring to FIG. 7, step 702 involves monitoring for a wakeup notice (e.g., a wakeup pulse) using the LF receiver 120 coupled to the first electrode 501 (e.g., the distal tip electrode 108*a*) and the third electrode 503 (e.g., the proximal electrode 108*b*) while the HF receiver 122 is disabled and the second electrode 502 (e.g., the fixation element 205) is electrically disconnected from the first electrode 501 (e.g., the distal tip electrode 108*a*). Step 704 involves determining whether the wakeup notice has been received. If the answer to the determination at step 704 is No, then flow returns to step 702, and step 702 is repeated. If the answer to step 704 is Yes, then flow goes to step 706.

Step 706 involves using a switch Sw to electrically connect the second electrode 502 (e.g., the fixation element) to the first electrode 501 (e.g., the distal tip electrode 108*a*). Step 708 involves enabling the HF receiver 122. The order of steps 706 and 708 can be reversed, or steps 706 and 708 can be performed at the same time, so long as steps 707 and 708 are performed response to the wakeup notice being received.

Step 710 involves receiving payload data (that follows the wakeup notice) using the HF receiver 122 that is coupled to the first electrode 501 (e.g., the distal tip electrode 108*a*) and the third electrode 503 (e.g., the proximal electrode 108*b*), while the first electrode 501 (e.g., the distal tip electrode 108*a*) is electrically connected to the second electrode 502 (e.g., the fixation element 205) by the switch Sw.

After the payload data is received at step 710, step 712 involves using the switch Sw to electrically disconnect the second electrode 502 (e.g., the fixation element 205) from the first electrode 501 (e.g., the distal tip electrode 108*a*). Flow then returns to step 702. While not specifically shown in FIG. 7, between steps 712 and a next instance of step 702, a further step can be performed that involves delivering one or more stimulation pulses (produced by a pulse generator 116) using the first electrode 501 (e.g., the distal tip electrode 108*a*) and the third electrode 503 (e.g., the proximal electrode 108*b*), while the second electrode 502 (e.g., the fixation element 205) is electrically disconnected from the first electrode 501 (e.g., the distal tip electrode 108*a*) by the switch Sw.

Figure 8:
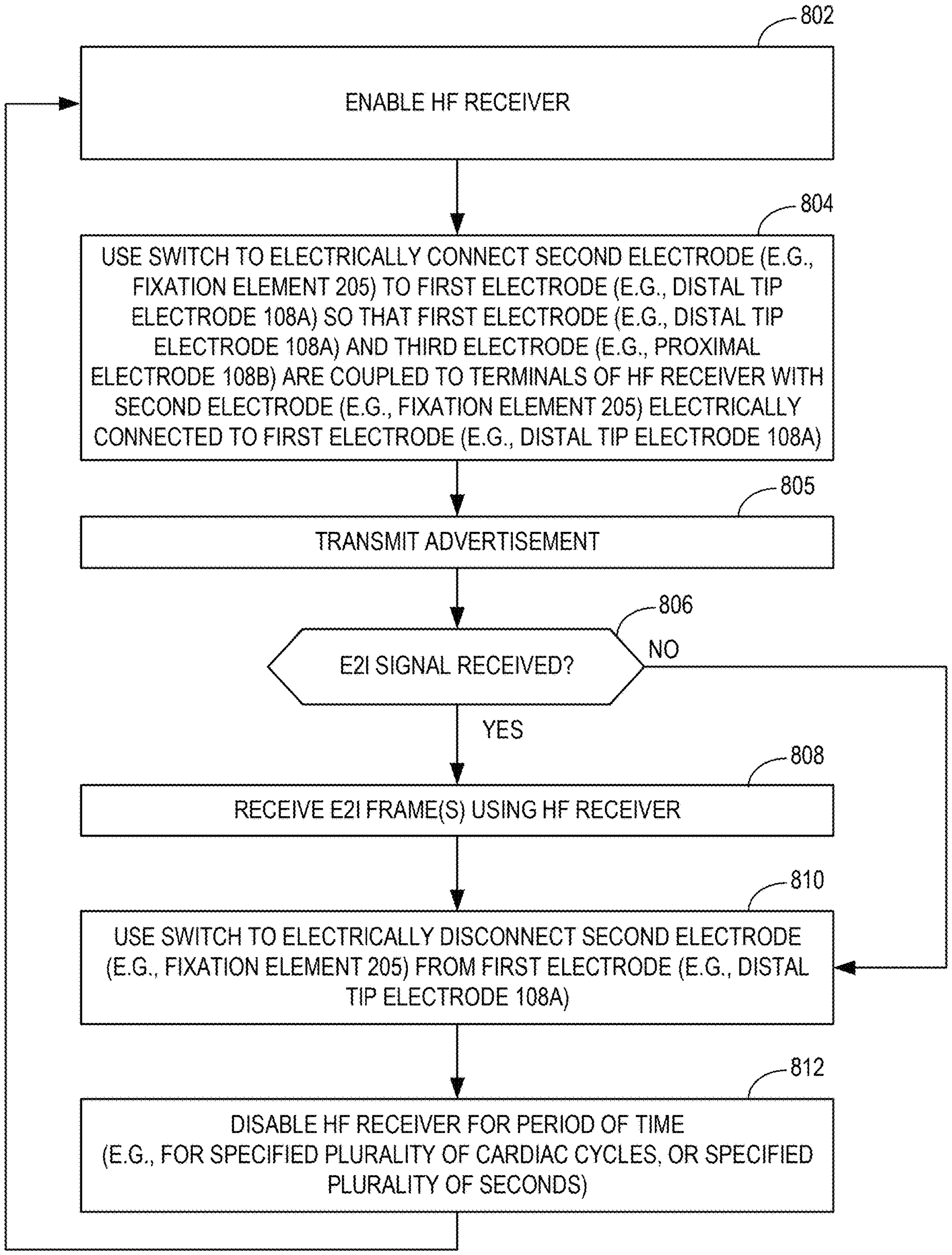
FIG. 8 is a high level flow diagram used to summarize methods according to certain embodiments of the present technology that are used by an implantable leadless biostimulator to receive e2i conductive communication signals.

The high level flow diagram of FIG. 8 will now be used to summarize methods according to certain embodiments of the present technology that are used by an implantable leadless biostimulator (e.g., LP 102) that includes both a LF receiver (e.g., 120) and a HF receiver (e.g., 122), examples of which were described above with reference to FIG. 1B to receive e2i conductive communication signals from an external device (e.g., 109). Step 802 involves enabling the HF receiver 122. Step 804 involves using the switch Sw to electrically connect the second electrode 502 (e.g., the fixation element 205) to the first electrode 501 (e.g., the distal tip electrode 108*a*) so that the first electrode 501 (e.g., the distal tip electrode) and the third electrode 503 (e.g., the proximal electrode 108*b*) are coupled to inputs of the HF receiver 122 while the second electrode 502 (e.g., the fixation element 205) is electrically connected to the first electrode 501 (e.g., the distal tip electrode 108*a*).

At step 805 the implantable leadless biostimulator (e.g., LP 102) transmits an advertisement, which can be a known sequence, so that an external device 109 (e.g., an external programmer, or a remote monitor) that has or is communicatively coupled to external electrodes 115*a*, 115*b* that are in contact with the patient (within the leadless biostimulator is implanted) can detect the presence of the implantable leadless biostimulator (e.g., LP 102) and optionally establish an active conductive telemetry session (which can also be referred to as an active conductive communication session) with the implantable leadless biostimulator (e.g., LP 102).

At step 806 there is a determination of whether an e2i signal, and more specifically an open link command in response to the advertisement, is received. If the answer to the determination at step 806 is Yes, then one or more e2i frames is/are received at step 808, and then flow goes to step 810. If the answer to the determination at step 806 is No, the flow goes to step 810 without any e2i frame being received. At step 812 the HF receiver 122 is disabled for a period of time, e.g., a specified plurality of cardiac cycles (e.g., 8 cardiac cycles), or a specified number of seconds (e.g., 5 seconds), and then flow returns to step 802.

In accordance with certain embodiments, during the conductive i2i, e2i, and i2e communication, pulse peak voltage is kept relatively constant (approximately the device battery voltage). For a single i2i or i2e pulse, the transmission power can be approximated using the following equation:

$$P = \frac{V_{batt}^2}{R_{tissue}}$$

where

P is the transmission power, $V_{batt}$ is the battery voltage, and $R_{tissue}$ is the tissue resistance.

As can be appreciated from the above equation, transmission power of i2i and i2e pulses increases by decreasing the tissue resistance (aka tissue impedance). Therefore, the total tissue impedance can be optimized for conductive telemetry versus battery longevity by controlling the conductive surface area of second electrode (e.g., the fixation element) with partial insulation coating.

An aspect of the present technology is directed to an implantable leadless biostimulator 102 comprising first, second and third electrodes 501, 502, 503. Each of the first and the second electrodes 501, 502 is located on and/or extending from a distal portion of the implantable leadless biostimulator 102 and is configured such that a respective electrically conductive surface area thereof is configured to be in physical contact with patient tissue of a patient within which the implantable leadless biostimulator is to be implanted, and such that the electrically conductive surface area of the second electrode 502 that is configured to be in physical contact with the patient tissue is greater than the electrically conductive surface area of the first electrode 501 that is configured to be in physical contact with the patient tissue. The third electrode 503 is located on a proximal portion of the implantable leadless biostimulator 102 and electrically isolated from the first and the second electrodes 501, 502. The implantable leadless biostimulator 102 further comprises circuitry 103 configured to cause a first set of the electrodes, which includes the first electrode 501 and the third electrode 503, but does not include the second electrode 502, to be used during first periods of time to deliver stimulation pulses to the patient tissue. The circuitry 103 is also configured to cause a second set of the electrodes, which includes the second electrode 502 and the third electrode 503, to be used during second periods of time to at least one of transmit conductive communication pulses to, or receive conductive communication pulses from, one or more other devices 104, 106, 109 (and/or another implantable leadless biostimulator 102). The second set of electrodes optionally includes the first electrode 501 electrically connected to the second electrode 502.

Explained another way, the circuitry 103 is configured to cause delivery of stimulation pulses to the patient tissue during first periods of time by a first set of the electrodes, which includes the first electrode 501 and the third electrode 503, but does not include the second electrode 502; and to cause transmission of conductive communication pulses to, and/or reception of conductive communication pulses from, one or more other devices 104, 106, 109 (and/or another implantable leadless biostimulator 102) during second periods of time by a second set of the electrodes, which includes the second electrode 502 and the third electrode 503. In such embodiments, the second set of electrodes optionally includes the first electrode 501 electrically connected to the second electrode 502.

In accordance with certain embodiments, the first electrode 501 comprises a distal tip electrode **108*a* located at a distal end of the implantable leadless biostimulator 102; the second electrode 502 comprises a fixation element 205 extending from the distal portion of the implantable leadless biostimulator 102 and configured to physically attach the implantable leadless biostimulator 102 to the patient tissue, or the second electrode 502 comprises a distal ring electrode 215 that encircles the distal tip electrode 108*a*; and the third electrode 503 comprises a proximal electrode 108*b* located on the proximal portion of the implantable leadless biostimulator 102**.

In accordance with certain embodiments, a first portion of the distal tip electrode **108*a*** is covered by an insulator coating and a second portion of the distal tip electrode is devoid of the insulator coating in order to achieve a higher effective impedance than would be achieved if an entirety of the distal tip electrode were devoid of the insulator coating.

In accordance with certain embodiments, the implantable leadless biostimulator 102 further comprises a battery 114 configured to power the implantable leadless biostimulator 102 including the circuitry 103 thereof; wherein the second electrode 502 comprises the fixation element 205; and wherein a first portion of the fixation element 205 is covered by an insulator coating and a second portion of the fixation element 205 is devoid of the insulator coating in order to achieve an effective impedance (e.g., within a specified range) that increases a longevity of the battery compared to if an entirety of the fixation element was devoid of the insulator coating.

In accordance with certain embodiments, the proximal electrode **108*b* is provided by at least a portion of an electrically conductive housing 110, 202 that houses the battery 114; and the distal tip electrode 108*a* is electrically isolated from the electrically conductive housing 110, 202**.

In accordance with certain embodiments, the implantable leadless biostimulator 102 is a leadless pacemaker; the distal tip electrode **108*a* is located at a distal end of the leadless pacemaker and is configured to be in physical contact with cardiac tissue; the second electrode 502 comprises the fixation element 205, which is configured to physically attach the leadless pacemaker to the cardiac tissue; the proximal electrode 108*a* is located on a proximal portion of the leadless pacemaker; and the electrically conductive surface area of the fixation element 205 that is configured to be in physical contact with the cardiac tissue is greater than the electrically conductive surface area of the distal tip electrode 108*a*** that is configured to be in physical contact with the cardiac tissue.

In accordance with certain embodiments, the first set of the electrodes includes the distal tip electrode **108*a* and the proximal electrode 108*b*; and the second set of electrodes includes the fixation element 205 or the distal ring electrode 215 electrically connected to the distal tip electrode 108*a*, and also includes the proximal electrode 108*b***.

In accordance with certain embodiments, the circuitry 103 comprises a controller 112 and a switch Sw; the controller 112 is configured to: control the switch Sw to cause the first electrode 501 and the second electrode 502 to be electrically disconnected from one another during the first periods of time during which stimulation pulses are to be delivered to the patient tissue using the first electrode 501 and the third electrode 503; and control the switch Sw to cause the first electrode 503 and the second electrode 502 be electrically connected to one another during the second periods of time during which conductive communication pulses are to be at least one of transmitted to, or received from, the one or more other devices using the first electrode 501 and the second electrode 502, which are electrically connected to one another, and using the third electrode 503.

In accordance with certain embodiments, the implantable leadless biostimulator 102 further comprises a pulse generator 116 that is configured to produce both the stimulation pulses and the conductive communication pulses, wherein the circuitry 103 comprises a controller 112 and a switch Sw. The controller 112 is configured to control the switch Sw to cause the first electrode and the third electrode to be electrically connected to output terminals of the pulse generator 116 during the first periods of time during which stimulation pulses are to be delivered to the patient tissue using the first electrode 501 and the third electrode 503. The controller 112 is also configured to control the switch Sw to cause the second electrode 502 and the third electrode 503 to be electrically connected to the output terminals of the pulse generator 116 during the second periods of time during which the conductive communication pulses produced by the pulse generator 116 are to be transmitted to the one or more other devices using the second electrode 502 and the third electrode 503.

In accordance with certain embodiments, the implantable leadless biostimulator 102 further comprises: a first pulse generator **116*a* configured to produce the stimulation pulses; and a second pulse generator 116*b* configured to produce the conductive communication pulses. The circuitry 103 includes a controller 112 configured to selectively activate each of the first and the second pulse generators 116*a*, 116*b*. The first electrode 501 and the third electrode 503 are configured to deliver the stimulation pulses produced by the first pulse generator 116*a*. The second electrode 502 and the third electrode 503 are configured to transmit the conductive communication pulses produced by the second pulse generator 116*b*. The circuitry also comprises a switch Sw. The controller 112 is configured to: control the switch Sw to cause the second electrode 502 to be electrically disconnected from the first electrode 501 during the first periods of time during which the stimulation pulses are to be delivered to the patient tissue using the first 501 electrode and the third electrode 503; and control the switch Sw to cause the second electrode 502 to be electrically connected to the first electrode 501 during the second periods of time during which the conductive communication pulses are to be at least one of transmitted to, or received from, the one or more other devices using the first electrode 501 and the second electrode 502, which are electrically connected to one another, and using the third electrode 503**.

In accordance with certain embodiments, the implantable leadless biostimulator further comprises a LF receiver 120 and a HF receiver 122. The HF receiver 122 is normally disabled to conserve power. The LF receiver 120 is configured to monitor for a LF wakeup pulse in a signal sensed between the first electrode 501 and the third electrode 503 and in response to receiving the LF wakeup pulse the LF receiver 120 is configured to enable the HF receiver 122 so that the HF receiver 122 can receive HF conductive communication pulses from one of the one or more other devices. The circuitry includes a controller 112 and a switch Sw. The controller 112 is configured to control the switch Sw to cause the second electrode 502 to be electrically disconnected from the first electrode 501 while the LF receiver 120 monitors the signal sensed between the first electrode 501 and the third electrode 503 for the LF wakeup pulse from one of the one or more other devices. The controller 112 is also configured to control the switch Sw to cause the second electrode 502 to be electrically connected to the first electrode 501, in response to the LF receiver 120 receiving the LF wakeup pulse and enabling the HF receiver 122 so that the HF receiver 122 can receive HF conductive communication pulses from the one of the one or more other devices in a signal sensed between the first electrode 501 and the third electrode 503 while the second electrode 502 is electrically connected by the switch Sw to the first electrode 501.

In accordance with certain embodiments, the one or more other devices comprises an external device 109. The controller 112 is configured to: control the switch Sw to electrically connect the second electrode 502 to the first electrode 501 while monitoring for one or more conductive communication pulses transmitted by the external device 109 and while at least one frame is being conductively communicated between the implantable leadless biostimulator 102 and the external device 109. The controller 112 is also configured to control the switch Sw to electrically disconnect the second electrode 502 from the first electrode 501 while not monitoring for the one or more conductive communication pulses transmitted by the external device 109 and while no frame is being conductively communicated between the implantable leadless biostimulator 102 and the external device 109.

In accordance with certain embodiments, the implantable leadless biostimulator 102 is a leadless neurostimulator.

Another aspect of the present technology is directed to a method for use by an implantable leadless biostimulator 102 comprising first, second and third electrodes 501, 502, 503, wherein each of the first and the second electrodes 501, 502 is located on and/or extending from a distal portion of the implantable leadless biostimulator 102 and is configured such that a respective electrically conductive surface area thereof is configured to be in physical contact with patient tissue of a patient within which the implantable leadless biostimulator is implanted, and such that the electrically conductive surface area of the second electrode 502 that is configured to be in physical contact with the patient tissue is greater than the electrically conductive surface area of the first electrode 501 that is configured to be in physical contact with the patient tissue. The third electrode 503 is located on a proximal portion of the implantable leadless biostimulator and is electrically isolated from the first and the second electrodes 501, 502.

In accordance with certain embodiments, the method comprises: using a first set of the electrodes, which includes the first electrode 501 and the third electrode 503, but does not include the second electrode 502, during first periods of time to deliver stimulation pulses to the patient tissue; and using a second set of the electrodes, which includes the second electrode 502 and the third electrode 503, during second periods of time to at least one of transmit conductive communication pulses to, or receive conductive communication pulses from, one or more other devices. The second set of electrodes optionally includes the first electrode 501 electrically connected to the second electrode 502.

Explained another way, the method includes delivering stimulation pulses to the patient tissue during first periods of time by a first set of the electrodes, which includes the first electrode 501 and the third electrode 503, but does not include the second electrode 502; and transmitting conductive communication pulses to, and/or receiving conductive communication pulses from, one or more other devices during second periods of time by a second set of the electrodes, which includes the second electrode 502 and the third electrode 503. In such embodiments, the second set of electrodes optionally includes the first electrode 501 electrically connected to the second electrode 502.

In accordance with certain embodiments, the first electrode comprises a distal tip electrode located at a distal end of the implantable leadless biostimulator; the second electrode comprises a fixation element extending from the distal portion of the implantable leadless biostimulator and configured to physically attach the implantable leadless biostimulator to the patient tissue, or the second electrode comprises a distal ring electrode that encircles the distal tip electrode; and the third electrode comprises a proximal electrode located on the proximal portion of the implantable leadless biostimulator.

In accordance with certain embodiments, a first portion of the distal tip electrode is covered by an insulator coating and a second portion of the distal tip electrode is devoid of the insulator coating in order to achieve a higher effective impedance than would be achieved if an entirety of the distal tip electrode were devoid of the insulator coating.

In accordance with certain embodiments, the implantable leadless biostimulator is a leadless pacemaker; the distal tip electrode is located at a distal end of the leadless pacemaker and is configured to be in physical contact with cardiac tissue; the second electrode comprises the fixation element which is configured to physically attach the leadless pacemaker to the cardiac tissue; the proximal electrode is located on a proximal portion of the leadless pacemaker; and the electrically conductive surface area of the fixation element that is in physical contact with the cardiac tissue is greater than the electrically conductive surface area of the distal tip electrode that is in physical contact with the cardiac tissue.

In accordance with certain embodiments, the first set of the electrodes includes the distal tip electrode and the proximal electrode; and the second set of electrodes includes the fixation element or the distal ring electrode electrically connected to the distal tip electrode, and also includes the proximal electrode.

In accordance with certain embodiments, the method further comprises controlling a switch to cause the first electrode and the second electrode to be electrically disconnected from one another during the first periods of time during which stimulation pulses are to be delivered to the patient tissue using the first electrode and the third electrode; and controlling the switch to cause the first electrode and the second electrode to be electrically connected to one another during the second periods of time during which conductive communication pulses are to be at least one of transmitted to, or received from, the one or more other devices using the first electrode and the second electrode, which are electrically connected to one another, and using the third electrode.

In accordance with certain embodiments, the implantable leadless biostimulator further comprises a pulse generator that is configured to produce both the stimulation pulses and the conductive communication pulses, and the method further comprises: controlling a switch to cause the first electrode and the third electrode to be electrically connected to output terminals of the pulse generator during the first periods of time during which stimulation pulses are to be delivered to the patient tissue using the first electrode and the third electrode; and controlling the switch to cause the second electrode and the third electrode to be electrically connected to the output terminals of the pulse generator during the second periods of time during which the conductive communication pulses produced by the pulse generator are to be transmitted to the one or more other devices using the second electrode and the third electrode.

In accordance with certain embodiments, the implantable leadless biostimulator further comprises a first pulse generator configured to produce the stimulation pulses, and a second pulse generator configured to produce the conductive communication pulses, and the method further comprises: selectively activating each of the first and the second pulse generators; delivering the stimulation pulses produced by the first pulse generator using the first electrode and the third electrode; and transmitting the conductive communication pulses produced by the second pulse generator using the second electrode and the third electrode.

In accordance with certain embodiments, the method further comprises: controlling a switch to cause the first electrode and the second electrode to be electrically disconnected from one another during the first periods of time during which the stimulation pulses produced by the first pulse generator are to be delivered to the patient tissue using the first electrode and the third electrode; and controlling the switch to cause the first electrode and the second electrode to be electrically connected to one another during the second periods of time during which the conductive communication pulses produced by the second pulse generator are to be transmitted to the one or more other devices using the first electrode and the second electrode, which are electrically connected to one another, and using the third electrode.

In accordance with certain embodiments, the implantable leadless biostimulator of includes a LF receiver, and a HF receiver, wherein the HF receiver is normally disabled to conserve power, wherein the LF receiver is configured to monitor for a LF wakeup pulse and in response to receiving the LF wakeup pulse enable the HF receiver so that the HF receiver can receive HF conductive communication pulses from one of the one or more other devices. The method further comprises: controlling a switch to cause the first electrode and the second electrode to be electrically disconnected from one another while the LF receiver of the implantable leadless biostimulator monitors a signal sensed between the first electrode and the third electrode for the LF wakeup pulse from one of the one or more other devices; and controlling the switch to cause the first electrode and the second electrode to be electrically connected to one another, in response to the LF receiver receiving the LF wakeup pulse and enabling the HF receiver so that the HF receiver can receive HF conductive communication pulses from the one of the one or more other devices in a signal sensed between the first electrode and the third electrode while the first electrode and the second electrode are electrically connected by the switch to one another.

In accordance with certain embodiments, the one or more other devices comprises an external device, and the method further comprises: controlling a switch to electrically connect the first electrode and the second electrode to one another while monitoring for one or more conductive communication pulses transmitted by the external device and while at least one frame is being conductively communicated between the implantable leadless biostimulator and the external device; and controlling the switch to electrically disconnect the first electrode and the second electrode from one another while not monitoring for the one or more conductive communication pulses transmitted by the external device and while no frame is being conductively communicated between the implantable leadless biostimulator and the external device.

In accordance with certain embodiments, the implantable leadless biostimulator with which the method is used is a leadless neurostimulator.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the various flow diagrams. It would also be possible to just perform a subset of the steps shown in the various flow diagrams. For another example, it is possible to change the boundaries of some of the block diagrams.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms “including” and “in which” are used as the plain-English equivalents of the respective terms “comprising” and “wherein.” Moreover, in the following claims, the terms “first,” “second,” and “third,” etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase “means for” followed by a statement of function void of further structure.

What is claimed is:

1. An implantable leadless biostimulator, comprising:

first, second and third electrodes;

each of the first and the second electrodes located on and/or extending from a distal portion of the implantable leadless biostimulator and configured such that a respective electrically conductive surface area thereof is configured to be in physical contact with patient tissue of a patient within which the implantable leadless biostimulator is to be implanted, and such that the electrically conductive surface area of the second electrode that is configured to be in physical contact with the patient tissue is greater than the electrically conductive surface area of the first electrode that is configured to be in physical contact with the patient tissue;

the third electrode located on a proximal portion of the implantable leadless biostimulator and electrically isolated from the first and the second electrodes; and circuitry configured to cause a first set of the electrodes, which includes the first electrode and the third electrode, but does not include the second electrode, to be used during first periods of time to deliver stimulation pulses to the patient tissue; and a second set of the electrodes, which includes the second electrode and the third electrode, to be used during second periods of time to at least one of transmit conductive communication pulses to, or receive conductive communication pulses from, one or more other devices;

wherein the second set of electrodes optionally includes the first electrode electrically connected to the second electrode.

2. The implantable leadless biostimulator of claim 1, wherein:

the first electrode comprises a distal tip electrode located at a distal end of the implantable leadless biostimulator;

the second electrode comprises a fixation element extending from the distal portion of the implantable leadless biostimulator and configured to physically attach the implantable leadless biostimulator to the patient tissue, or the second electrode comprises a distal ring electrode that encircles the distal tip electrode; and the third electrode comprises a proximal electrode located on the proximal portion of the implantable leadless biostimulator.

3. The implantable leadless biostimulator of claim 2, wherein a first portion of the distal tip electrode is covered by an insulator coating and a second portion of the distal tip electrode is devoid of the insulator coating in order to achieve a higher effective impedance than would be achieved if an entirety of the distal tip electrode were devoid of the insulator coating.

4. The implantable leadless biostimulator of claim 2, further comprising:

a battery configured to power the implantable leadless biostimulator including the circuitry thereof;

wherein the second electrode comprises the fixation element; and wherein a first portion of the fixation element is covered by an insulator coating and a second portion of the fixation element is devoid of the insulator coating in order to achieve an effective impedance that increases a longevity of the battery compared to if an entirety of the fixation element was devoid of the insulator coating.

5. The implantable leadless biostimulator of claim 4, wherein:

the proximal electrode is provided by at least a portion of an electrically conductive housing that houses the battery; and the distal tip electrode is electrically isolated from the electrically conductive housing.

6. The implantable leadless biostimulator of claim 2, wherein:

the implantable leadless biostimulator is a leadless pacemaker;

the distal tip electrode is located at a distal end of the leadless pacemaker and is configured to be in physical contact with cardiac tissue;

the second electrode comprises the fixation element, which is configured to physically attach the leadless pacemaker to the cardiac tissue;

the proximal electrode is located on a proximal portion of the leadless pacemaker; and the electrically conductive surface area of the fixation element that is configured to be in physical contact with the cardiac tissue is greater than the electrically conductive surface area of the distal tip electrode that is configured to be in physical contact with the cardiac tissue.

7. The implantable leadless biostimulator of claim 2, wherein:

the first set of the electrodes includes the distal tip electrode and the proximal electrode; and the second set of electrodes includes the fixation element or the distal ring electrode electrically connected to the distal tip electrode, and also includes the proximal electrode.

8. The implantable leadless biostimulator of claim 2, wherein:

the circuitry comprises a controller and a switch;

the controller is configured to:

control the switch to cause the first electrode and the second electrode to be electrically disconnected from one another during the first periods of time during which stimulation pulses are to be delivered to the patient tissue using the first electrode and the third electrode; and control the switch to cause the first electrode and the second electrode be electrically connected to one another during the second periods of time during which conductive communication pulses are to be at least one of transmitted to, or received from, the one or more other devices using the first electrode and the second electrode, which are electrically connected to one another, and using the third electrode.

9. The implantable leadless biostimulator of claim 1, wherein:
the circuitry comprises a controller and a switch;
the controller is configured to:
control the switch to cause the first electrode and the second electrode to be electrically disconnected from one another during the first periods of time during which stimulation pulses are to be delivered to the patient tissue using the first electrode and the third electrode; and
control the switch to cause the first electrode and the second electrode be electrically connected to one another during the second periods of time during which conductive communication pulses are to be at least one of transmitted to, or received from, the one or more other devices using the first electrode and the second electrode, which are electrically connected to one another, and using the third electrode.

10. The implantable leadless biostimulator of claim 1, further comprising:
a pulse generator that is configured to produce both the stimulation pulses and the conductive communication pulses;
wherein the circuitry comprises a controller and a switch;
the controller is configured to
control the switch to cause the first electrode and the third electrode to be electrically connected to output terminals of the pulse generator during the first periods of time during which stimulation pulses are to be delivered to the patient tissue using the first electrode and the third electrode; and
control the switch to cause the second electrode and the third electrode to be electrically connected to the output terminals of the pulse generator during the second periods of time during which the conductive communication pulses produced by the pulse generator are to be transmitted to the one or more other devices using the second electrode and the third electrode.

11. The implantable leadless biostimulator of claim 1, further comprising:
a first pulse generator configured to produce the stimulation pulses; and
a second pulse generator configured to produce the conductive communication pulses;
wherein the circuitry includes a controller configured to selectively activate each of the first and the second pulse generators;
wherein the first electrode and the third electrode are configured to deliver the stimulation pulses produced by the first pulse generator; and
wherein the second electrode and the third electrode are configured to transmit the conductive communication pulses produced by the second pulse generator.

12. The implantable leadless biostimulator of claim 11, wherein:
the circuitry also comprises a switch;
the controller is configured to
control the switch to cause the second electrode to be electrically disconnected from the first electrode during the first periods of time during which the stimulation pulses are to be delivered to the patient tissue using the first electrode and the third electrode; and
control the switch to cause the second electrode to be electrically connected to the first electrode during the second periods of time during which the conductive communication pulses are to be at least one of transmitted to, or received from, the one or more other devices using the first electrode and the second electrode, which are electrically connected to one another, and using the third electrode.

13. The implantable leadless biostimulator of claim 1, further comprising:
a low frequency (LF) receiver; and
a high frequency (HF) receiver;
wherein the HF receiver is normally disabled to conserve power;
wherein the LF receiver is configured to monitor for a LF wakeup pulse in a signal sensed between the first electrode and the third electrode and in response to receiving the LF wakeup pulse the LF receiver is configured to enable the HF receiver so that the HF receiver can receive HF conductive communication pulses from one of the one or more other devices; and
wherein the circuitry includes a controller and a switch; and
wherein the controller is configured to:
control the switch to cause the second electrode to be electrically disconnected from the first electrode while the LF receiver monitors the signal sensed between the first electrode and the third electrode for the LF wakeup pulse from one of the one or more other devices; and
control the switch to cause the second electrode to be electrically connected to the first electrode, in response to the LF receiver receiving the LF wakeup pulse and enabling the HF receiver so that the HF receiver can receive HF conductive communication pulses from the one of the one or more other devices in a signal sensed between the first electrode and the third electrode while the second electrode is electrically connected by the switch to the first electrode.

14. The implantable leadless biostimulator of claim 13, wherein:
the one or more other devices comprises an external device;
the controller is configured to
control the switch to electrically connect the second electrode to the first electrode while monitoring for one or more conductive communication pulses transmitted by the external device and while at least one frame is being conductively communicated between the implantable leadless biostimulator and the external device; and
control the switch to electrically disconnect the second electrode from the first electrode while not monitoring for the one or more conductive communication pulses transmitted by the external device and while no frame is being conductively communicated between the implantable leadless biostimulator and the external device.

15. The implantable leadless biostimulator of claim 1, the implantable leadless biostimulator is a leadless neurostimulator.

16. A method for use by an implantable leadless biostimulator comprising first, second and third electrodes, wherein each of the first and the second electrodes is located on and/or extending from a distal portion of the implantable leadless biostimulator and is configured such that a respective electrically conductive surface area thereof is configured to be in physical contact with patient tissue of a patient within which the implantable leadless biostimulator is implanted, and such that the electrically conductive surface area of the second electrode that is configured to be in physical contact with the patient tissue is greater than the electrically conductive surface area of the first electrode that is configured to be in physical contact with the patient tissue, and wherein the third electrode is located on a proximal portion of the implantable leadless biostimulator and electrically isolated from the first and the second electrodes, the method comprising:

using a first set of the electrodes, which includes the first electrode and the third electrode, but does not include the second electrode, during first periods of time to deliver stimulation pulses to the patient tissue; and using a second set of the electrodes, which includes the second electrode and the third electrode, during second periods of time to at least one of transmit conductive communication pulses to, or receive conductive communication pulses from, one or more other devices;

wherein the second set of electrodes optionally includes the first electrode electrically connected to the second electrode.

17. The method of claim 16, wherein:

the first electrode comprises a distal tip electrode located at a distal end of the implantable leadless biostimulator;

the second electrode comprises a fixation element extending from the distal portion of the implantable leadless biostimulator and configured to physically attach the implantable leadless biostimulator to the patient tissue, or the second electrode comprises a distal ring electrode that encircles the distal tip electrode; and the third electrode comprises a proximal electrode located on the proximal portion of the implantable leadless biostimulator.

18. The method of claim 17, wherein a first portion of the distal tip electrode is covered by an insulator coating and a second portion of the distal tip electrode is devoid of the insulator coating in order to achieve a higher effective impedance than would be achieved if an entirety of the distal tip electrode were devoid of the insulator coating.

19. The method of claim 17, wherein:

the implantable leadless biostimulator is a leadless pacemaker;

the distal tip electrode is located at a distal end of the leadless pacemaker and is configured to be in physical contact with cardiac tissue;

the second electrode comprises the fixation element which is configured to physically attach the leadless pacemaker to the cardiac tissue;

the proximal electrode is located on a proximal portion of the leadless pacemaker; and the electrically conductive surface area of the fixation element that is in physical contact with the cardiac tissue is greater than the electrically conductive surface area of the distal tip electrode that is in physical contact with the cardiac tissue.

20. The method of claim 17, wherein:

the first set of the electrodes includes the distal tip electrode and the proximal electrode; and the second set of electrodes includes the fixation element or the distal ring electrode electrically connected to the distal tip electrode, and also includes the proximal electrode.

21. The method of claim 16, further comprising:

controlling a switch to cause the first electrode and the second electrode to be electrically disconnected from one another during the first periods of time during which stimulation pulses are to be delivered to the patient tissue using the first electrode and the third electrode; and controlling the switch to cause the first electrode and the second electrode to be electrically connected to one another during the second periods of time during which conductive communication pulses are to be at least one of transmitted to, or received from, the one or more other devices using the first electrode and the second electrode, which are electrically connected to one another, and using the third electrode.

22. The method of claim 16, wherein the implantable leadless biostimulator further comprises a pulse generator that is configured to produce both the stimulation pulses and the conductive communication pulses, and wherein the method further comprises:

controlling a switch to cause the first electrode and the third electrode to be electrically connected to output terminals of the pulse generator during the first periods of time during which stimulation pulses are to be delivered to the patient tissue using the first electrode and the third electrode; and controlling the switch to cause the second electrode and the third electrode to be electrically connected to the output terminals of the pulse generator during the second periods of time during which the conductive communication pulses produced by the pulse generator are to be transmitted to the one or more other devices using the second electrode and the third electrode.

23. The method of claim 16, wherein the implantable leadless biostimulator further comprises a first pulse generator configured to produce the stimulation pulses, and a second pulse generator configured to produce the conductive communication pulses, and wherein the method further comprises:

selectively activating each of the first and the second pulse generators;

delivering the stimulation pulses produced by the first pulse generator using the first electrode and the third electrode; and transmitting the conductive communication pulses produced by the second pulse generator using the second electrode and the third electrode.

24. The method of claim 23, further comprising:

controlling a switch to cause the first electrode and the second electrode to be electrically disconnected from one another during the first periods of time during which the stimulation pulses produced by the first pulse generator are to be delivered to the patient tissue using the first electrode and the third electrode; and controlling the switch to cause the first electrode and the second electrode to be electrically connected to one another during the second periods of time during which the conductive communication pulses produced by the second pulse generator are to be transmitted to the one or more other devices using the first electrode and the second electrode, which are electrically connected to one another, and using the third electrode.

25. The method of claim 16, wherein the implantable leadless biostimulator of includes a low frequency (LF) receiver, and a high frequency (HF) receiver, wherein the HF receiver is normally disabled to conserve power, wherein the LF receiver is configured to monitor for a LF wakeup pulse and in response to receiving the LF wakeup pulse enable the HF receiver so that the HF receiver can receive HF conductive communication pulses from one of the one or more other devices, and wherein the method further comprises:

controlling a switch to cause the first electrode and the second electrode to be electrically disconnected from one another while the LF receiver of the implantable leadless biostimulator monitors a signal sensed between the first electrode and the third electrode for the LF wakeup pulse from one of the one or more other devices; and controlling the switch to cause the first electrode and the second electrode to be electrically connected to one another, in response to the LF receiver receiving the LF wakeup pulse and enabling the HF receiver so that the HF receiver can receive HF conductive communication pulses from the one of the one or more other devices in a signal sensed between the first electrode and the third electrode while the first electrode and the second electrode are electrically connected by the switch to one another.

26. The method of claim 16, wherein the one or more other devices comprises an external device, and wherein the method further comprises:

controlling a switch to electrically connect the first electrode and the second electrode to one another while monitoring for one or more conductive communication pulses transmitted by the external device and while at least one frame is being conductively communicated between the implantable leadless biostimulator and the external device; and controlling the switch to electrically disconnect the first electrode and the second electrode from one another while not monitoring for the one or more conductive communication pulses transmitted by the external device and while no frame is being conductively communicated between the implantable leadless biostimulator and the external device.

27. The method of claim 16, the implantable leadless biostimulator is a leadless neurostimulator.

* * * * *